United States Patent [19]
Jones

[11] 4,418,068
[45] Nov. 29, 1983

[54] ANTIESTROGENIC AND ANTIANDRUGENIC BENZOTHIOPHENES

[75] Inventor: Charles D. Jones, Indianapolis, Ind.

[73] Assignee: Eli Lilly and Company, Indianapolis, Ind.

[21] Appl. No.: 331,042

[22] Filed: Dec. 16, 1981

Related U.S. Application Data

[63] Continuation-in-part of Ser. No. 246,335, Apr. 3, 1981, abandoned.

[51] Int. Cl.$^3$ .................. A61K 31/445; C07D 409/12
[52] U.S. Cl. .................................. 424/267; 546/202; 546/237; 549/51
[58] Field of Search .................... 546/202; 424/267

[56] References Cited

U.S. PATENT DOCUMENTS

| | | | |
|---|---|---|---|
| 3,920,707 | 11/1975 | Descamps et al. | 546/196 X |
| 3,947,470 | 3/1976 | Brenner et al. | 424/275 X |
| 3,983,245 | 9/1976 | Ladd | 424/285 |
| 4,001,426 | 1/1977 | Brenner et al. | 424/285 |
| 4,075,227 | 2/1978 | Jones et al. | 260/330.5 |
| 4,133,814 | 1/1979 | Jones et al. | 260/326.55 |
| 4,230,862 | 10/1980 | Suarez et al. | 546/237 |

FOREIGN PATENT DOCUMENTS 819675 of 0000 Belgium .

OTHER PUBLICATIONS

Nicholson, R., et al., *Europ. J. Cancer*, 11, 571–579 (1975).
Ricciardi, I., et al., *Ob. and Gyn.*, 54 (1), 80–84 (1979).
Jacquemier, J., et al., *Cancer*, 49 (12), 2534–2536 (1982).
Coombs, L. et al., *Preven. Med.*, 8, 40–52 (1979).
Stoliar, B., et al., *J. Urology*, 111, 803–807 (1974).
Sogani, P., et al., *J. Urology*, 122, 640–643 (1979).
Caine, M., et al., *J. Urology*, 114, 564–568 (1975).
Geller, J., et al., *Geriatrics*, 63–71 (1977).
Ward, H., *Br. Med. J.*, 1, 13–14 (1973).
Jordan, V., et al., *J. Endocr.*, 68, 305–311 (1976).
Black, L., in *Hormone Antagonists* (Agarwal, Ed.), W. DeGruyter, New York, 1982, pp. 129–145.
Claeys, N. et al., *Chimie Therapeutique*, 377–384 (1972).
Black, L., et al., *Life Sciences* 26, 1453–1458 (1980).
Lednicer, D., et al., *J. Med. Chem.* 10, 78–83 (1967).

*Primary Examiner*—Richard A. Schwartz
*Attorney, Agent, or Firm*—Joseph A. Jones; Arthur R. Whale

[57] ABSTRACT

6-Hydroxy-2-(4-hydroxyphenyl)-3-[4-(2-piperidinoethoxy)benzoyl]benzo[b]thiophene, its ethers and esters, and the physiologically acceptable acid addition salts thereof, are valuable antiestrogens and antiandrogens.

62 Claims, No Drawings

ANTIESTROGENIC AND ANTIANDRUGENIC BENZOTHIOPHENES

CROSS-REFERENCE

This application is a continuation-in-part of application Ser. No. 246,335, filed Apr. 3, 1981, now abandoned.

BACKGROUND OF THE INVENTION

1. Field of the Invention

This invention relates to the field of biochemistry, and provides pharmaceutical agents which are antiestrogens and antiandrogens.

Estrogen is transported throughout the body in the bloodstream and passively enters cells. However, only certain tissues exhibit responses to the hormone and are accordingly designated target tissues. These target tissues are characterized by specific estrogen receptors. The interaction of estradiol with estrogen receptors is an early event in a complex series of events which result in an estrogenic response. The uterus is considered the primary target tissue for estrogen. It is rich in estrogen receptors and exhibits dramatic growth under the influence of estradiol. Consequently the uterotropic response of rodents provides a reproducible model for the evaluation of estrogenic and antiestrogenic activity as well as the study of interactions with estrogen receptors.

A relationship has been established between estrogen sensitivity or dependency and the occurrence of estrogen receptors in certain mammary cancers as well as in benign fibrocystic disease of the breast. The neutralization of estrogen influence on those tissues is expected to benefit patients with those conditions by causing regression or preventing recurrence of the condition.

Antiestrogens antagonize the action of estrogens in animal models and display clinical efficacy in most mammary cancers which contain estrogen receptors. They interact with estrogen receptors, and elicit partial estrogenic response. Thus, the ability to antagonize the effect of estradiol is related to and restricted by the degree of intrinsic estrogenicity of the compound. The compound that evokes the greatest degree of estrogen antagonism, accordingly, is expected to be the most beneficial.

Similarly, androgen circulates and is taken up by androgen-receptive tissues. Prostatic cancer is a clinical condition believed to have androgen dependency or sensitivity, as does the condition known as benign prostatic hypertrophy. Accordingly, anti-androgens are in demand, and anti-androgenic testing is successfully carried out based on the rapid growth of the rodent prostate under the influence of androgen.

2. State of the Art

Antiestrogens have been under investigation for some years, and at least one such compound is presently being sold for palliative cancer therapy. This drug is tamoxifen, 1-(4-β-dimethylaminoethoxyphenyl)-1,2-diphenylbut-1-ene.

Another group of known antiestrogens are the dihydronaphthalenes of U.S. Pat. No. 4,230,862, of Suarez and Jones. The most important compound of this group is trioxifene mesylate, 2-[4-(2-pyrrolidinoethoxy)-benzoyl]-1-(4-methoxyphenyl)-3,4-dihydronaphthalene, methanesulfonic acid salt. Trioxifene has been clinically tested in cases of advanced breast cancer.

Another group of antiestrogens are the benzothiophenes of Jones and Suarez, U.S. Pat. No. 4,133,814. Tests of one of their compounds, 6-hydroxy-2-(4-hydroxyphenyl)-3-[4-(2-pyrrolidinoethoxy)benzoyl]-benzo[b]thiophene, have been published by Black and Goode, Life Sciences 26, 1453–58 (1980). The same article also discussed similar tests of tamoxifen and trioxifene as estrogens and antiestrogens. The authors concluded that the above benzothiophene was considerably more effective as an antiestrogen, and considerably less estrogenic, than either tamoxifen or trioxifene.

SUMMARY OF THE INVENTION

This invention provides 6-hydroxy-2-(4-hydroxyphenyl)-3-[4-(2-piperidinoethoxy)benzoyl]benzo[b]thiophene, having the formula

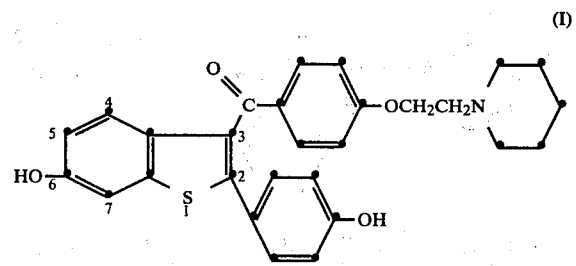

the physiologically acceptable esters and ethers thereof, and the physiologically acceptable acid addition salts thereof.

The compounds are antiestrogens and antiandrogens, and are used as pharmaceuticals for antiestrogen and antiandrogen therapy, especially in the treatment of mammary and prostatic tumors and in the treatment and prophylaxis of mammary and prostatic fibrocystic disease. Accordingly, pharmaceutical compositions and methods of antiestrogenic and anti-androgenic therapy are important parts of the invention. More particularly, the invention provides a method of alleviating a pathological condition of an endocrine target organ, which condition is dependent or partially dependent on an estrogen or on an androgen, which comprises administering an effective dose of a compound as described above to a subject suffering from such a condition or at risk of suffering from such a condition.

DESCRIPTION OF THE PREFERRED EMBODIMENTS

This invention provides a single benzothiophene compound and the physiologically acceptable esters and ethers which are formed on one or both of the hydroxy groups of the compound. The invention also provides physiologically acceptable salts of the compound in any of its forms.

Pharmaceutical chemists will easily recognize that physiologically active compounds which have accessible hydroxy groups are frequently administered in the form of physiologically acceptable esters or ethers. The literature concerning such compounds, such as estradiol, provides a great number of instances of such esters and ethers. The compound of this invention is no exception in this respect, but can be effectively administered as an ether or ester, formed on either one or both of the hydroxy groups, just as one skilled in pharmaceutical chemistry would expect. While the mechanism has not yet been investigated, it is believed that ethers and esters are metabolically cleaved in the body, and that the actual drug, when such a form is administered, is the dihydroxy compound itself. It is possible, as has long been known in pharmaceutical chemistry, to adjust the rate or duration of action of the compound by appropriate choices of ester or ether groups. For example, the cycloalkyl ethers are known to increase the duration of action of many hydroxy-group-bearing physiologically active compounds.

Certain ether and ester groups are preferred as constituents of the compounds of this invention. The following formula shows the dihydroxy compound and the preferred ether and ester compounds.

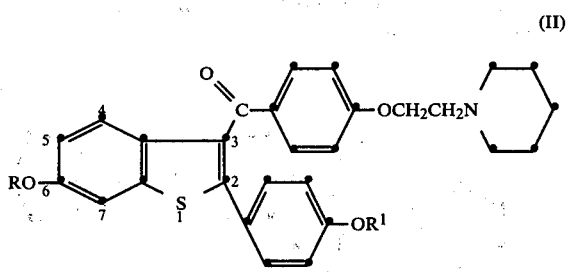

(II)

wherein R and $R^1$ independently are hydrogen, —$COR^2$ or $R^3$;

$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl;

$R^3$ is $C_1$–$C_4$ alkyl, $C_5$–$C_7$ cycloalkyl or benzyl; and the physiologically acceptable acid addition salts thereof.

In this document, all measurements are expressed in weight units, unless otherwise stated, except that ratios of solvents are expressed in volume units.

The general chemical terms used in the formulae above have their usual meanings. For example, the terms $C_1$–$C_{14}$ alkyl, $C_1$–$C_4$ alkoxy and $C_1$–$C_4$ alkyl include groups such as methyl, ethyl, isopropyl, butyl, s-butyl, tetradecyl, undecyl, neopentyl, 2,2-dimethylhexyl, 3-ethylnonyl, 3-butylheptyl, dodecyl, methoxy, propoxy and i-butoxy.

The terms $C_1$–$C_3$ chloroalkyl and $C_1$–$C_3$ fluoroalkyl include methyl, ethyl, propyl and isopropyl substituted to any desired degree with chlorine or fluorine atoms, from one atom to full substitution. The term $C_5$–$C_7$ cycloalkyl includes cyclopentyl, cyclohexyl and cycloheptyl.

The physiologically acceptable acid addition salts of the compounds of this invention may be formed of the dihydroxy compound itself, or of any of its esters or ethers, and include the physiologically acceptable salts which are often used in pharmaceutical chemistry. For example, salts may be formed with inorganic or organic acids such as hydrobromic acid, hydriodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferably with hydrochloric acid, citric acid, benzoic acid, maleic acid, acetic acid and propionic acid. It is usually preferred to administer a compound of this invention in the form of an acid addition salt, as is customary in the administration of pharmaceuticals bearing a basic group such as the piperidino ring.

A group of representative compounds according to the invention will be mentioned by name, to assure that the reader of this document fully understands the compounds.

6-hydroxy-2-(4-hydroxyphenyl)-3-[4-(2-piperidinoethoxy)benzoyl]benzo[b]thiophene, hydrochloride 6-hydroxy-2-(4-hydroxyphenyl)-3-[4-(2-piperidinoethoxy)benzoyl]benzo[b]thiophene, citrate 6-hydroxy-2-(4-hydroxyphenyl)-3-[4-(2-4-piperidinoethoxy)benzoyl]benzo[b]thiophene, lactate 6-hydroxy-2-(4-hydroxyphenyl)-3-[4-(2-piperidinoethoxy)benzoyl]benzo[b]thiophene, sulfonate 6-hydroxy-2-(4-hydroxyphenyl)-3-[4-(2-piperidinoethoxy)benzoyl]benzo[b]thiophene, hydrogen sulfate 6-hydroxy-2-(4-hydroxyphenyl)-3-[4-(2-piperidinoethoxy)benzoyl]benzo[b]thiophene, acetate 6-hydroxy-2-(4-hydroxyphenyl)-3-[4-(2-piperidinoethoxy)benzoyl]benzo[b]thiophene, methanesulfonate 6-formyloxy-2-(4-formyloxyphenyl)-3-[4-(2-piperidinoethoxy)benzoyl]benzo[b]thiophene, hydrochloride 6-acetoxy-2-(4-acetoxyphenyl)-3-[4-(2-piperidinoethoxy)benzoyl]benzo[b]thiophene, hydrobromide 6-hydroxy-2-(4-propionyloxyphenyl)-3-[4-(2-piperidinoethoxy)benzoyl]benzo[b]thiophene, nitrate 2-(4-hydroxyphenyl)-6-valeryloxy-3-[4-(2-piperidinoethoxy)benzoyl]benzo[b]thiophene, sulfate 2-(4-hydroxyphenyl)-6-(2,2-dimethylpropionyloxy)-3-[4-(2-piperidinoethoxy)benzoyl]benzo[b]thiophene, toluenesulfonate 6-hydroxy-2-(4-heptanoyloxyphenyl)-3-[4-(2-piperidinoethoxy)benzoyl]benzo[b]thiophene, methanesulfonate 6-(2,3-dimethylbutyryloxy)-2-[4-(2,3-dimethylbutyryloxy)phenyl]-3-[4-(2-piperidinoethoxy)-benzoyl]-benzo[b]thiophene, lactate 6-nonanoyloxy-2-(4-nonanoyloxyphenyl)-3-[4-(2-piperidinoethoxy)benzoyl]benzo[b]thiophene, dihydrogen phosphate 6-acetoxy-2-(4-undecanoyloxyphenyl)-3-[4-(2-piperidinoethoxy)benzoyl]benzo[b]thiophene, phosphate 2-(4-hydroxyphenyl)-6-tridecanoyloxy-3-[4-(2-piperidinoethoxy)benzoyl]benzo[b]thiophene, metaphosphate 2-(4-benzoyloxyphenyl)-6-pentadecanoyloxy-3-[4-(2-piperidinoethoxy)benzoyl]benzo[b]thiophene, hydriodide 6-(2-methylpropionyloxy)-2-[4-(2-methylpropionyloxy)phenyl]-3-[4-(2-piperidinoethoxy)benzoyl]-benzo[b]thiophene, sulfonate 6-hydroxy-2-[4-(3-ethylhexanoyloxy)phenyl]-3-[4-(2-piperidinoethoxy)benzoyl]benzo[b]thiophene, acetate 6-(2-propylvaleryloxy)-2-[4-(2-propylvaleryloxy)phenyl]-3-[4-(2-piperidinoethoxy)benzoyl]benzo[b]thiophene, propionate 6-hydroxy-2-[4-(2,2-diethylheptanoyloxy)phenyl]-3-[4-(2-piperidinoethoxy)benzoyl]benzo[b]thiophene, formate 2-(4-propionyloxyphenyl)-6-(3-propylnonanoyloxy)-3-[4-(2-piperidinoethoxy)benzoyl]benzo[b]thiophene, phthalate 6-hydroxy-2-[4-(5-butylundecanoyloxy)phenyl]-3-[4-(2-piperidinoethoxy)benzoyl]benzo[b]thiophene 2-(4-hydroxyphenyl)-6-trifluoroacetoxy-3-[4-(2-piperidinoethoxy)benzoyl]benzo[b]thiophene, hydrochloride 2-(4-butyryloxyphenyl)-6-trichloroacetoxy-3-[4-(2-piperidinoethoxy)benzoyl]benzo[b]thiophene, hydriodide 2-(4-hydroxyphenyl)-6-(3,3,3-trifluoropropionyloxy)-3-[4-(2-piperidinoethoxy)benzoyl]benzo[b]thiophene 6-(3-chloropropionyloxy)-2-[4-(3-chloropropionyloxy)phenyl]-3-[4-(2-piperidinoethoxy)benzoyl]benzo[b]thiophene, lactate 6-hydroxy-2-[4-(2,3-dichlorobutyryloxy)phenyl]-3-[4-(2-piperidinoethoxy)benzoyl]benzo[b]thiophene 2-[4-(2,3,4-trifluorobutyryloxy)phenyl]-6-(4-methoxybenzoyloxy)-3-[4-(2-piperidinoethoxy)benzoyl]-benzo[b]thiophene 6-pentafluoropropionyloxy-2-(4-pentafluoropropionyloxyphenyl)-3-[4-(2-piperidinoethoxy)benzoyl]benzo[b]thiophene, citrate 6-heptachlorobutyryloxy-2-(4-heptachlorobutyryloxyphenyl)-3-[4-(2-piperidinoethoxy)benzoyl]-benzo[b]thiophene 6-cyclopentylcarbonyloxy-2-(4-cyclopentylcarbonyloxyphenyl)-3-[4-(2-piperidinoethoxy)benzoyl]benzo[b]thiophene, toluenesulfonate 6-acetoxy-2-(4-cyclohexylcarbonyloxyphenyl)-3-[4-(2-piperidinoethoxy)benzoyl]benzo[b]thiophene 6-hydroxy-2-(4-cycloheptylcarbonyloxyphenyl)-3-[4-(2-piperidinoethoxy)benzoyl]benzo[b]thiophene 2-(4-hydroxyphenyl)-6-methoxycarbonyloxy-3-[4-(2-piperidinoethoxy)benzoyl]benzo[b]thiophene, tartrate 6-benzoyloxy-2-(4-ethoxycarbonyloxyphenyl)-3-[4-(2-piperidinoethoxy)benzoyl]benzo[b]thiophene, phthalate 2-(4-hydroxyphenyl)-6-propoxycarbonyloxy-3-[4-(2-piperidinoethoxy)benzoyl]benzo[b]thiophene, hydrobromide 2-(4-hydroxyphenyl)-6-isobutoxycarbonyloxy-3-[4-(2-piperidinoethoxy)benzoyl]benzo[b]thiophene, sulfate 6-ethoxy-2-(4-t-butoxycarbonyloxyphenyl)-3-[4-(2-piperidinoethoxy)benzoyl]benzo[b]thiophene 6-benzoyloxy-2-(4-benzoyloxyphenyl)-3-[4-(2-piperidinoethoxy)benzoyl]benzo[b]thiophene, nitrate 6-(4-methylbenzoyloxy)-2-[4-(4-methylbenzoyloxy)phenyl]-3-[4-(2-piperidinoethoxy)benzoyl]benzo[b]thiophene 6-hydroxy-2-[4-(2,4-diethylbenzoyloxy)phenyl]-3-[4-(2-piperidinoethoxy)benzoyl]benzo[b]-thiophene, metaphosphate 6-hydroxy-2-[4-(3-methyl-5-propylbenzoyloxy)phenyl]-3-[4-(2-piperidinoethoxy)benzoyl]benzo[b]-thiophene, picrate 6-(2,5-dibutylbenzoyloxy)-2-(4-methoxyphenyl)-3-[4-(2-piperidinoethoxy)benzoyl]benzo[b]thiophene, acetate 2-(4-hydroxyphenyl)-6-(4-methoxybenzoyloxy)-3-[4-(2-piperidinoethoxy)benzoyl]benzo[b]thiophene, propionate 6-(3-isopropoxybenzoyloxy)-2-[4-(3-isopropoxybenzoyloxy)phenyl]-3-[4-(2-piperidinoethoxy)benzoyl]benzo[b]thiophene 2-(4-hydroxyphenyl)-6-(4-t-butoxybenzoyloxy)-3-[4-(2-piperidinoethoxy)benzoyl]benzo[b]thiophene 6-benzoyloxy-2-[4-(3,5-diethoxybenzoyloxy)phenyl]-3-[4-(2-piperidinoethoxy)benzoyl]benzo[b]-thiophene, formate 6-(4-hydroxybenzoyloxy)-2-[4-(4-hydroxybenzoyloxy)phenyl]-3-[4-(2-piperidinoethoxy)benzoyl]-benzo[b]thiophene, methanesulfonate 6-(2,4-dihydroxybenzoyloxy)-2-[4-(2,4-dihydroxybenzoyloxy)phenyl]-3-[4-(2-piperidinoethoxy)-benzoyl]benzo[b]thiophene 2-(4-hydroxyphenyl)-6-(2,4-dinitrobenzoyloxy)-3-[4-(2-piperidinoethoxy)benzoyl]benzo[b]thiophene, lactate 6-(3-chlorobenzoyloxy)-2-(4-hydroxyphenyl)-3-[4-(2-piperidinoethoxy)benzoyl]benzo[b]thiophene, toluenesulfonate 6-cyclopentoxy-2-[4-(2,4-dichlorobenzoyloxy)phenyl]-3-[4-(2-piperidinoethoxy)benzoyl]benzo[b]-thiophene, methanesulfonate 2-(4-hydroxyphenyl)-6-(2,5-difluorobenzoyloxy)-3-[4-(2-piperidinoethoxy)benzoyl]benzo[b]thiophene 6-hydroxy-2-[4-(2-trifluoromethylbenzoyloxy)phenyl]-3-[4-(2-piperidinoethoxy)benzoyl]benzo[b]thiophene, hydrochloride 2-(4-acetoxyphenyl)-6-[3,5-bis(trichloromethyl)benzoyloxy]-3-[4-(2-piperidinoethoxy)benzoyl]benzo[b]thiophene, hydrochloride 6-methoxy-2-(4-methoxyphenyl)-3-[4-(2-piperidinoethoxy)benzoyl]benzo[b]thiophene 6-ethoxy-2-(4-ethoxyphenyl)-3-[4-(2-piperidinoethoxy)benzoyl]benzo[b]thiophene, formate 6-hydroxy-2-(4-isopropoxyphenyl)-3-[4-(2-piperidinoethoxy)benzoyl]benzo[b]thiophene, succinate 6-hydroxy-2-(4-butoxyphenyl)-3-[4-(2-piperidinoethoxy)benzoyl]benzo[b]thiophene, hydrochloride 6-s-butoxy-2-(4-methoxyphenyl)-3-[4-(2-piperidinoethoxy)benzoyl]benzo[b]thiophene 2-(4-hydroxyphenyl)-6-cyclopentoxy-3-[4-(2-piperidinoethoxy)benzoyl]benzo[b]thiophene, hydriodide 6-hydroxy-2-(4-cyclohexyloxyphenyl)-3-[4-(2-piperidinoethoxy)benzoyl]benzo[b]thiophene 2-(4-cycloheptyloxyphenyl)-6-propionyloxy-3-[4-(2-piperidinoethoxy)benzoyl]benzo[b]thiophene, formate 6-benzyloxy-2-(4-benzyloxyphenyl)-3-[4-(2-piperidinoethoxy)benzoyl]benzo[b]thiophene Certain classes of the compounds of this invention are preferred. The following paragraphs describe such preferred classes.

(a) R and $R^1$ are the same;
(b) one of R and $R^1$ is hydrogen;
(c) one or both of R and $R^1$ is —$COR^2$;
(d) one or both of R and $R^1$ is $R^3$;
(e) $R^2$ is alkyl;
(f) $R^2$ is chloroalkyl or fluoroalkyl;
(g) $R^2$ is cycloalkyl;
(h) $R^2$ is alkoxy;
(i) $R^2$ is phenyl;
(j) $R^2$ is substituted phenyl;
(k) $R^3$ is alkyl;
(l) $R^3$ is cycloalkyl;
(m) $R^3$ is benzyl;
(n) the compound is a free base;
(o) the compound is a salt;
(p) the compound is a hydrochloride.

It will be understood that the above classes may be combined to form additional preferred classes.

The compounds of this invention are made by a process which conveniently starts with a benzo[b]thiophene having a 6-hydroxy group and a 2-(4-hydroxyphenyl) group.

The starting compound is protected, acylated and deprotected to form the desired dihydroxy compound.

Biologically active ethers and esters may then be formed if desired. Other variations of the process are also conveniently used and will be explained below.

Protection

The first step in the usual synthesis is to protect the hydroxy groups, as indicated below.

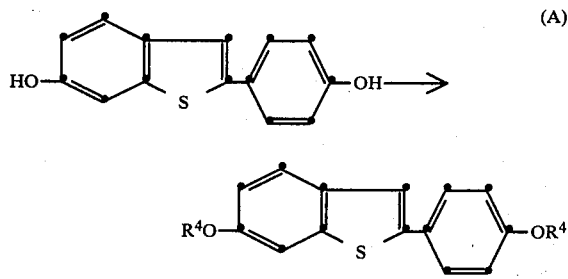

(A)

wherein $R^4$ is $R^3$, $-COR^5$ or $-SO_2R^5$; $R^5$ is $C_1-C_4$ primary or secondary alkyl, $C_1-C_3$ fluoroalkyl, $C_1-C_3$ chloroalkyl, $C_1-C_4$ alkylphenyl, $C_1-C_4$ alkoxyphenyl, mono- or dinitrophenyl or mono- or di(chloro or fluoro)phenyl.

Alternatively, the 2-phenylbenzothiophene may be formed with $R^3$ protecting groups in place on the compound as it is synthesized, as illustrated below in Preparation 6. The $R^3$ groups are then kept in place on the compound throughout the process, as illustrated further below in Example 8.

The $-COR^5$ and $-SO_2R^5$ groups are placed on the dihydroxy compound according to methods known in the art. For example, when a $-COR^5$ group is desired, the dihydroxy compound is reacted with an acylating agent such as an acyl chloride, bromide, cyanide or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine or the like. The reaction may also be carried out in an inert solvent such as ethyl acetate, dimethylformamide, dimethylsulfoxide, dioxane, dimethoxyethane, acetonitrile, acetone, methyl ethyl ketone or the like, to which at least one equivalent of an acid scavenger, such as a tertiary amine, has been added. Acylation catalysts such as 4-dimethylaminopyridine or 4-pyrrolidinopyridine may be used, if desired. See, in general, Haslam, Tetrahedron 36, 2409-33 (1980). The acylation reactions which provide $-COR^5$ groups are carried out at moderate temperatures in the range of from $-25°$ C. to $100°$ C.

Such acylations of the hydroxy groups may also be performed by acid-catalyzed reactions of the appropriate carboxylic acids, in inert organic solvents or neat. Acid catalysts such as sulfuric acid, polyphosphoric acid, methanesulfonic acid and the like are used.

The $-COR^5$ groups may also be provided by forming an active ester of the appropriate acid, such as the esters formed by such known reagents as dicyclohexylcarbodiimide, acylimidazoles, nitrophenols, pentachlorophenol, N-hydroxysuccinimide and 1-hydroxybenzotriazole. See, for example, Bul. Chem. Soc. Japan 38, 1979 (1965), and Chem. Ber., 788 and 2024 (1970).

Other techniques are also known, such as by means of mixed anhydrides of the phosphorus compounds, Shioiri and Hamada, J. Org. Chem. 43, 3631-32 (1978); the use of 2-haloheterocyclic compounds such as 2-chloropyridine, Narasaka et al., Chem. Let., 763-66 (1977); and the use of thiol esters.

All of the above techniques of acylations which provide $-COR^5$ groups are carried out in solvents as discussed above. Those techniques which do not produce an acid product in the course of the reaction, of course, do not call for an acid scavenger in the reaction mixture.

Still other acylation methods are also useful, such as the use of an $R^5$-substituted ketene in an inert solvent, as discussed above, at a low temperature in the range of $-30°$ C. to $25°$ C. Still further, the dihydroxy compound can be first converted to its dianion by treatment with a very strong base such as sodium hydroxide, sodium methoxide, potassium hydride, sodium hydride, n-butyllithium or the like, in order to obtain more complete reaction with the reagents which have been mentioned above. Acylation by the dianion technique is carried out in an inert solvent as described above, with no additional base or catalyst. The temperature of reactions according to the dianion technique is from $-30°$ C. to $50°$ C.

When a $-SO_2R^5$-protected compound is desired, the dihydroxy starting compound is reacted with, for example, a derivative of the appropriate sulfonic acid, such as a sulfonyl chloride, bromide or sulfonyl ammonium salt, as taught by King and Manoir, J. Am. Chem. Soc. 97, 2566-67 (1975). The dihydroxy compound can also be reacted with the appropriate sulfonic anhydride. Such reactions are carried out under conditions such as were explained above in the discussion of reactions with acyl halides and the like.

The $-SO_2R^5$ groups may also be provided by reaction of the dihydroxy compound with an appropriately substituted sulfene under conditions as discussed above for reactions with substituted ketenes. Still further, any of the sulfonate-producing reactions may be carried out on a dihydroxy compound in the dianion form, as discussed above.

It should be noted that the $R^3$ and $-COR^5$ groups used as protecting groups are within the scope of preferred biologically active groups, as discussed above, and thus it is entirely practical to use a given group as a protecting group in the synthesis, and to keep it in place on the product as an active ether or ester.

Acylation

The protected starting compound is acylated as the second step in the usual synthesis. The acylation can be done either with an acylating agent already containing the piperidinoethoxy group of the desired product, or with a precursor of it, as shown below.

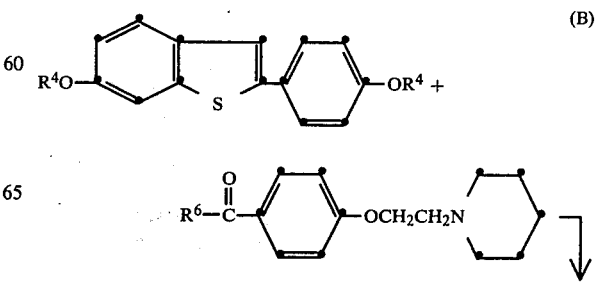

(B)

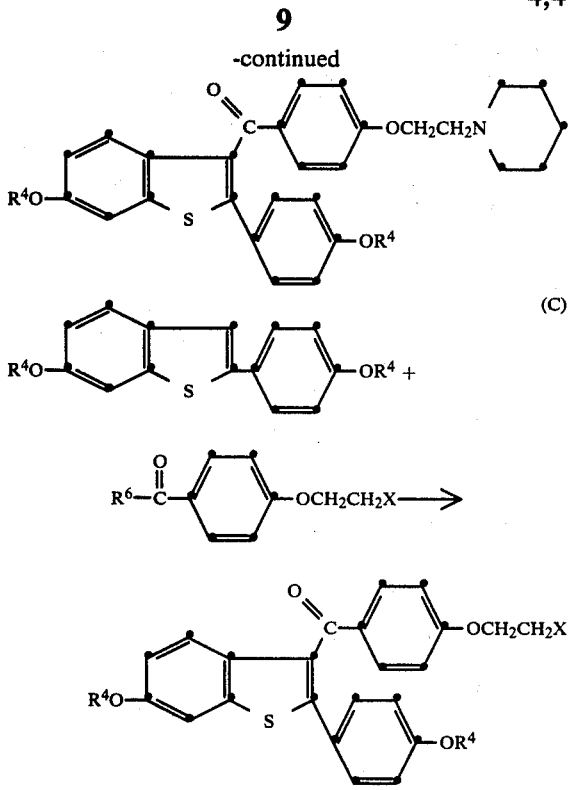

wherein X is bromo, chloro, iodo or —OSO$_2$R$^5$. The acylating agents are discussed in detail below.

The acylation of reactions B and C is a Friedel-Crafts acylation, and is carried out in the usual way. Either a Lewis acid or a proton acid may be used as the Friedel-Crafts catalyst; an excellent discussion of such catalysts appears in Olah, Friedel-Crafts and Related Reactions, Interscience Publ., New York, London and Sidney, 1963, vol. I, Ch. III and IV.

As explained by Olah, the classical Friedel-Crafts catalysts were Lewis acids. Such metal halides as aluminum chloride, aluminum bromide, zinc chloride, boron trifluoride, boron trichloride, boron tribromide, titanium tetrachloride, titanium tetrabromide, stannic chloride, stannic bromide, bismuth trichloride and ferric chloride are well known catalysts and are useful in this acylation, especially for acylations of reaction B. This proton acid catalysts are also useful for this acylation, especially for acylations of reaction C, and include such substances as phosphoric acid, polyphosphoric acid, perchloric acid, chlorosulfonic acid, alkylsulfonic acids such as methanesulfonic and ethanesulfonic acids, toluenesulfonic and benzenesulfonic acids, sulfuric acid, chloroacetic acid and trifluoroacetic acid. It is preferred to carry out the acylation with aluminum chloride or trifluoromethanesulfonic acid.

The acylation is ordinarily carried out in a solvent, and any inert organic solvent which is not significantly attacked by the conditions may be used. For example, halogenated solvents such as dichloromethane, 1,2-dichloroethane, chloroform and the like may be used, as can aromatics such as benzene, chlorobenzene and the like, alkanes such as petroleum ether, hexane and the like, and nitrohydrocarbons such as nitrobenzene and nitroalkanes.

It has been found that toluene is rather easily acylated under the conditions used in the Friedel-Crafts acylation step, and so it is important, when toluene is used in an earlier step of the process, to remove it as completely as possible from the protected starting compound, to avoid wasting the acylating agent.

The acylations may be carried out at temperatures from about the ambient temperature to about 100° C., preferably at the reflux temperature of the reaction mixture for processes catalyzed with the preferred proton acid, trifluoromethanesulfonic acid, and preferably at about ambient temperature for Lewis acid catalyzed processes.

The acylating agent used in the acylations B and C is an active form of the appropriate benzoic acid, wherein R$^6$ is one of the recognized "active groups", such as a chlorine atom, a bromine atom, or an activating ester. Appropriate activating esters are formed, as is well known, with hydroxybenzotriazole, dicyclohexylcarbodiimide and the like. The group R$^6$ may also indicate an anhydride, especially a mixed anhydride such as those formed with small carboxylic acids such as acetic acid, formic acid and especially sulfonic acids.

It is preferred, when the basic side chain is added according to reaction B above, to use as the acylating agent a small excess (1.05-1.5 molar) of the proper benzoyl halide, and to use, as the Friedel-Crafts catalyst, a slight molar excess of trifluoromethanesulfonic acid, or, alternatively, fluorosulfonic acid, p-toluenesulfonic acid, a dihalophosphoric acid or concentrated sulfuric acid. Alternatively, the reaction is also carried out in a preferred manner by using a substantial excess (1.5 to 3.5 molar) of the benzoyl halide in the presence of a large excess (2-12 molar) of aluminum chloride; other Lewis acid catalysts, such as aluminum bromide and the like may also be used.

In the case of acylations according to reaction C above, it is preferred to carry out the acylation in the presence of a strong acid such as was discussed immediately above. In this reaction, a full equivalent of acid is not necessary; a catalytic amount of acid is adequate. It is preferred to carry out the acylation steps in an inert halogenated solvent such as chloroform, dichloromethane, benzene, 1,2-dichloroethane and the like. In general, see as to such acylation reactions an article by Effenberger, Agnew. Chem. Int. Ed. Engl. 19, 151–230, especially 163–65 (1980).

Displacement

When the starting compound is acylated according to reaction C above, the piperidino group of the product is subsequently put in place by displacing the X group with piperidine. The X groups are leaving groups, which are easily displaced by an amine such as piperidine according to known methods.

For example, the displacement is carried out in an inert solvent such as ketones in the nature of acetone or methyl ethyl ketone, esters such as ethyl acetate and propyl formate, alcohols such as methanol or ethanol, nitriles such as acetonitrile, or amides such as dimethylacetamide and dimethylformamide, or in such inert solvents as hexamethylphosphoramide, and in the presence of an acid scavenger such as alkali metal carbonates and bicarbonates and the like. At least an equimolar quantity of acid scavenger is needed, and preferably a moderate excess. The displacement is carried out at ambient temperature, or may be carried out at moderately elevated temperatures from about ambient temperature to the reflux temperature of the reaction mixture.

More preferably, the displacement may be carried out in the additional presence of a catalytic amount of iodide ion, which acts as a catalyst for the displacement. When iodide is used in the mixture, the temperature range is lower, from about 0° C. to, preferably, the ambient temperature, although elevated temperatures are possible in some instances.

Further, the anion of piperidine may be formed before the reaction is carried out, as by contact with a very strong base such as sodium hydride or an alkyllithium compound. The use of an anion does not otherwise change the manner in which the displacement is carried out, except that an acid scavenger is not needed.

Deprotection

When a dihydroxy compound of this invention, of formula I above, is needed, it is obtained by cleaving the protecting groups, $R^4$, from the acylated compounds. Deprotection is carried out after displacement, when the 2-step acylation-displacement route is used. Both acyl and sulfonyl-protected compounds have been deprotected by simple hydrolysis with strong or moderately strong bases. For example, bases such as alkali metal hydroxides may be used for the hydrolysis, at temperatures from about the ambient temperature to about 100° C. At least two equivalents of base are needed, of course. Such hydrolyses are conveniently carried out in hydroxylic solvents, especially aqueous alkanols. The reactions may be also carried out, however, in any convenient solvent which leads itself to hydrolysis reactions, such as polyols including ethylene glycol, ethers such as tetrahydrofuran and the like, ketones such as acetone and methyl ethyl ketone and other polar water-miscible solvents such as dimethylsulfoxide. A preferred solvent system is a mixture of methanol and tetrahydrofuran, at ambient temperature. The cleavage may also be carried out with other bases, including, for example, sodium methoxide, potassium t-butoxide, hydrazine, hydroxylamine, ammonia, alkali metal amides and secondary amines such as diethylamine and the like. In some instances, when very strong bases are used, reaction temperatures in the range of from about 0° C. to the ambient temperature will give adequately rapid reaction rates.

The hydrolysis step lends itself well to reaction with the base in a 2-phase system with the assistance of a phase transfer catalyst. Such catalysts are now well known and are found among the tetraalkyl ammonium halides and among the crown ethers, such as dicyclohexyl-18-crown-6 ether.

In the case of compounds protected with —$COR^5$ groups, hydrolysis is readily carried out with acid catalysts, such as methanesulfonic acid, hydrochloric acid, hydrobromic acid, sulfuric acid, a mixture of hydrobromic acid/acetic acid, or with acidic ion exchange resins. Such acid-catalyzed hydrolyses are carried out in hydroxylic solvents, such as water, alkanols, aqueous alkanols, or a mixture of tetrahydrofuran/methanol. It is preferred to carry out such hydrolyses at about the reflux temperature of the mixture, but, when particularly strong acids are used, temperatures as low as the ambient temperature are efficient.

A partially hydrolyzed compound is often desired, where only one of the hydroxy groups is deprotected. Such compounds may be prepared by any of the hydrolytic methods described above, by limiting the amount of base or the time of the reaction, or by lowering the temperature, so as to obtain less than complete hydrolysis. Such procedure usually produces a mixture of partially hydrolyzed compounds, which are separated by chromatography.

Basic hydrolysis in a primary or secondary alcohol solvent has been found to produce a relatively small amount of a mixture of compounds wherein one of the hydroxy groups has been hydrolyzed, and the other has been converted to an alkyl ether where the alkyl group is derived from the alcohol solvent. The major product of the reaction is the dihydroxy compound. Such monoethers are compounds of this invention, wherein one of R and $R^1$ is hydrogen and the other is an $R^3$ alkyl group derived from the alcohol.

When the starting compound was protected with $R^3$ alkyl, cycloalkyl or benzyl groups, the protecting groups are removed by known ether cleavage methods, most preferably in the presence of ethanethiol and aluminum chloride, as illustrated below in Example 8.

It has been found that the steps of displacement and cleavage of the protecting groups, $R^4$, can be combined to produce the dihydroxy compound in one step from an intermediate having a leaving group, X, on the side chain. Example 7 below illustrates such a step. The intermediate having the X group on the side chain is dissolved in a solvent which is suitable for processing at high temperature. Dimethylformamide is a particularly suitable solvent, as also is dimethylacetamide. Other solvents can be used as well, such as high-molecular-weight alkanes and halogenated alkanes having high boiling points. The intermediate is dissolved in the solvent, and piperidine is added, preferably with a catalytic amount of an iodide salt or a phase transfer catalyst to assist in the displacement reaction. The reaction mixture is stirred for a short time, such as a few hours, which serves to displace —X, and the mixture is then heated to an elevated temperature in the range of about 100°–150° C., with appropriate stirring, and preferably under an inert gas atmosphere. The $R^4$ protecting groups then hydrolyze to produce the desired dihydroxy compound in a single step.

Ethers and Esters

When it is desired to prepare a compound of this invention wherein one or both of R and $R^1$ is an ether group, the ether is prepared by placing the $R^3$ moiety on one or both of the hydroxy groups in a manner commonly used for the preparation of ethers. For example, the $R^3$ group may be added by reaction with an appropriate diazo compound, such as diazomethane, phenyldiazomethane or trimethylsilyldiazomethane (see Hashimoto et al., Tet. Let., 4619–22 (1980).) Such reactions are effectively carried out in solvents including esters such as ethyl acetate, halogenated solvents including dichloromethane and chloroform, and ethers including diethyl ether and tetrahydrofuran. Methanol or boron trifluoride is used as a catalyst, and the process is usually carried out at low temperatures from about −45° C. to about 0° C. Alternatively, alkylations may be carried out with the assistance of reagents such as trimethyloxosulfonium hydroxide, trimethylsulfonium hydroxide and trimethylselenonium hydroxide (all of which provide methyl groups), as taught by Yamauchi, Tet. Let., 1787–90 (1979). Alkylations with these reagents are carried out in solvents which are conducive to $S_N2$ displacements such as dimethylsulfoxide, dimethylformamide, hexamethylphosphoramide, acetone, acetonitrile and the like, usually at elevated temperatures from about 40° C. to about the reflux temperature of the mixture.

Such alkylations may neatly be used to provide a mono-ether product, wherein one of R and $R^1$ is an $R^3$ alkyl group, by partially hydrolyzing the intermediate product, so that one of the $R^4$ protecting groups is left in place, alkylating, and completing the hydrolysis to remove the remaining $R^4$ group.

It is preferable, however, to prepare monoethers by using an ultimate starting compound in the mono-ether form, and using the ether group as a protecting group through the synthesis, protecting the other hydroxy with an acyl or sulfonyl group.

When a compound is desired wherein one or both of R and $R^1$ are $-COR^2$, it may often be most convenient to prepare the compound using an $R^4$ protecting group other than the desired $-COR^2$ group, hydrolyze off the protecting group and re-acylate one or both of the hydroxy groups at the end of the synthesis. Such acylations are carried out as described above in the discussion of $-COR^2$ groups as protecting groups. A particularly preferred condition for final acylations is to use tetrahydrofuran as the solvent and potassium carbonate as the acid scavenger for acylating agents such as acetic anhydride, benzyl chloride, ethyl chloroformate and the like. Another preferred reaction condition for very reactive acylating reagents such as trifluoroacetic anhydride is to use an equivalent of the corresponding acid (trifluoroacetic acid in the above instance) in tetrahydrofuran at about ambient temperature, and to add the acylating agent as the last addition to the reaction mixture.

Methyl-Protected Route

A particularly preferred route for preparing the dihydroxy compound of this invention is performed by preparing a dimethyl-protected benzothiophene starting compound, and acylating with the basic side chain according to a variation of reaction scheme B above. The methoxy groups are preferably cleaved with ethanethiol to prepare the dihydroxy compound in good yield, and without isolation of any of the intermediate products.

The methyl-protected starting compound is most easily obtained by a synthesis which is exemplified below in the first part of Preparation 6. The process is carried out by reacting 3-methoxybenzenethiol and α-bromo-4-methoxyacetophenone in the presence of a strong base at a relatively low temperature, to form α-(3-methoxyphenylthio)-4-methoxyacetophenone, which is then ring-closed with an agent such as polyphosphoric acid at a high temperature to obtain the desired starting compound.

The acylation is a Friedel-Crafts acylation, and is carried out in the usual way, using aluminum chloride or bromide, preferably the chloride, as the acylation catalyst.

The acylation is ordinarily carried out in a solvent, and any inert organic solvent which is not significantly attacked by the conditions may be used. For example, halogenated solvents such as dichloromethane, 1,2-dichloroethane, chloroform and the like may be used, as can aromatics such as benzene, chlorobenzene and the like. It is preferred to use a halogenated solvent, especially dichloromethane.

The acylations may be carried out at temperatures from about $-30°$ C. to about 100° C., preferably at about ambient temperature, in the range of about 15° C. to about 30° C.

The acylating agent is an active form of the appropriate benzoic acid, wherein $R^6$ is a chlorine or bromine atom. The preferred acylating agent is that wherein $R^6$ is chloro.

The acyl chloride used as an acylating agent may be prepared from the corresponding carboxylic acid by reaction with a typical chlorinating agent such as thionyl chloride. Care must be taken to remove any excess chlorinating agent from the acyl chloride, however. Most conveniently, the acyl chloride is formed in situ, and the excess chlorinating agent is distilled off under vacuum.

Th stoichiometric amounts of the benzothiophene and the acylating agent may be used effectively. If desired, a small excess of either reactant may be added to assure that the other is fully consumed.

It is preferred to use a large excess of the acylation catalyst, such as about 2–12 moles per mole of product, preferably about 5–10 moles.

The acylation is rapid. Economically brief reaction times such as from about 15 minutes to a few hours provide high yields of the acylated intermediate. Longer reaction times may be used if desired but are not usually advantageous. As usual, the use of lower reaction temperatures calls for relatively long times.

The acylation step is ended, and the demethylation step begun, by adding to the reaction mixture a sulfur compound chosen from methionine and compounds of the formula $R^7-S-R^8$, wherein $R^7$ is hydrogen or unbranched $C_1-C_4$ alkyl, and $R^8$ is $C_1-C_4$ alkyl or phenyl.

The sulphur compounds are, most preferably, the alkylthiols, such as methanethiol, ethanethiol, the preferred agent, isopropanethiol, butanethiol and the like; dialkyl sulfides, such as diethyl sulfide, butyl s-butyl sulfide, ethyl propyl sulfide, butyl isopropyl sulfide, dimethyl sulfide, methyl ethyl sulfide and the like; benzenethiol; methionine; and alkyl phenyl sulfides such as methyl phenyl sulfide, ethyl phenyl sulfide, butyl phenyl sulfide and the like.

It has been found that the demethylation goes best when a substantial excess amount of the sulfur compound is used, in the range of from about 4 to about 10 moles per mole of the starting benzothiophene. The process can be carried out, although less efficiently, with a smaller amount of the sulfur compound in the range of about 2 or 3 moles per mole of starting compound. It is also possible to use a small amount of the sulfur compound, such as 2 or 3 moles per mole of starting compound, and to improve the yield by the addition of about 1 to 3 moles of an alkali metal halide, such as sodium, potassium or lithium chloride, iodide or bromide. (A similar effect of sodium iodide is shown by Niwa et al., Tet. Let. 22, 4239–40 (1981)).

The demethylation reaction goes well at about ambient temperature, in the range of from about 15° C. to about 30° C., and such operation is preferred. However, the demethylation step may be carried out at temperatures in the range of from about $-30°$ C. to about 50° C. if it is desired to do so. Short reaction times in the range of about 1 hour have been found to be adequate.

After the product has been demethylated, it is recovered and isolated by conventional means. It is customary to add water to decompose the complex of the acylation catalyst; addition of dilute aqueous acid is advantageous. The product precipitates in many instances, or may be extracted with an organic solvent according to conventional methods.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

All of the above reaction steps give acceptable yields when the stoichiometric amounts of the reactants are used, except as noted in certain specific steps above. As is normally the case in organic chemistry, improved yields are given by the use of an excess amount of one of the reactants, and it is practical to use an excess amount of the cheaper or the more easily obtained reactant. For example, in the formation of the protected starting compounds, it is practical and economical to use an excess of the acylating or sulfonating agent, to assure complete reaction of the more expensive dihydroxy starting compound. Excesses in the range of from about 1% to about 25% are conveniently used, when an excess of one reactant is desired.

The following preparations and examples further illustrate the synthesis of the compounds of this invention. The products described below were identified by various standard analytical techniques as stated in the individual preparations and examples. Nuclear magnetic resonance (nmr) analyses were run on a 100 mHz instrument in deuterochloroform unless otherwise stated.

The first preparation following illustrates the synthesis of an active form of a typical carboxylic acid for subsequent use as an acylating agent.

Preparation 1

4-(2-piperidinoethoxy)benzoic acid, hydrochloride

A 183 g. portion of methyl 4-(2-piperidinoethoxy)-benzoate was dissolved in 600 ml. of methanol, and 200 ml. of 5 N sodium hydroxide was added. The mixture was stirred at ambient temperature for 48 hours, the solvent was evaporated, and the residue was dissolved in 1 liter of water. The solution was cooled to below 10° C., and was acidified with cold 6 N hydrochloric acid. The product crystallized, and was collected by filtration and washed with methanol at −40° C. The solids were recrystallized from 3400 ml. of methanol to obtain 167 g. of the expected product, m.p. 274°–277° C.

The next four preparations illustrate the synthesis of protected starting compounds having various $R^4$ groups.

Preparation 2

6-acetoxy-2-(4-acetoxyphenyl)benzo[b]thiophene

Forty g. of 6-hydroxy-2-(4-hydroxyphenyl)-benzo[b]thiophene was dissolved in 800 ml. of anhydrous pyridine, and 41.6 g. of acetic anhydride and 100 mg. of 4-dimethylaminopyridine were added. The mixture was allowed to stand overnight at ambient temperature, and was then evaporated to an oily residue under vacuum. The residue was slurried with 3 liters of water with vigorous stirring, and the crystals which precipitated were collected by filtration and washed thoroughly with water. The solids were then dried at 80° C. under vacuum to obtain 52.5 g. of the acetyl-protected intermediate, m.p. 208°–210° C.

Preparation 3

6-benzoyloxy-2-(4-benzoyloxyphenyl)benzo[b]-thiophene

The synthesis was carried out according to the process of Preparation 2, except that 51.1 g. of benzoyl chloride was used instead of acetic anhydride. The product was 73.7 g. of the expected benzoyl-protected intermediate product in the form of white crystals, m.p. 216°–218° C.

Preparation 4

6-methanesulfonyloxy-2-(4-methanesulfonyloxyphenyl)benzo[b]thiophene

Twenty g. of 6-hydroxy-2-(4-hydroxyphenyl)-benzo[b]thiophene was dissolved in 400 ml. of pyridine, together with 23.4 g. of methanesulfonyl chloride and 50 mg. of 4-dimethylaminopyridine. The mixture was stirred under a nitrogen blanket overnight at ambient temperature, and was then poured into 2 liters of water and stirred vigorously. The solids were collected by filtration, and washed successively with water, methanol and diethyl ether. The washed solids were then vacuum dried at 60° C. to obtain 32.5 g. of the desired intermediate product, m.p. 195°–197° C.

Preparation 5

6-benzenesulfonyloxy-2-(4-benzenesulfonyloxyphenyl)benzo[b]thiophene

The synthesis was carried out substantially according to Preparation 2 above, except that 64.1 g. of benzenesulfonyl chloride was used in place of acetic anhydride. The product was worked up as described in Preparation 2 to obtain 85 g. of the crude product, m.p. 138°–139° C., which was recrystallized twice from ¼ methanol/ethyl acetate to obtain purified intermediate product, m.p. 146°–148° C.

Preparation 6

6-hydroxy-2-(4-hydroxyphenyl)benzo[b]thiophene

A 100 g. portion of 3-methoxybenzenethiol and 39.1 g. of potassium hydroxide dissolved in 300 ml. of water were added to 750 ml. of denatured ethanol, and the flask was put in a cooling bath. A total of 164 g. of α-bromo-4-methoxyacetophenone was then added in small portions, and the mixture was stirred for 10 minutes in the cooling bath after the addition was complete and then for 3 hours at ambient temperature. The solvent was then evaporated off in vacuum, and 200 ml. of water was added. The mixture was extracted with ethyl acetate, and the organic layer was washed twice with water, twice with aqueous sodium bicarbonate solution, and twice with aqueous sodium chloride solution. The organic layer was then dried over magnesium sulfate, filtered and evaporated under vacuum to obtain 202 g. of crude α-(3-methoxyphenylthio)-4-methoxyacetophenone, which was recrystallized from methanol and washed with hexane to obtain 158 g. of purified product, m.p. 53° C.

A 124 g. portion of the above intermediate was added in small portions to 930 g. of polyphosphoric acid at 85°

C. The temperature rose to 95° C. during the addition, and the mixture was stirred at 90° C. for 30 minutes after the addition was complete, and was then stirred an additional 45 minutes while it cooled without external heating. One liter of crushed ice was then added to the mixture, and an external ice bath was applied to control the temperature while the ice melted and diluted the acid. Five hundred ml. of additional water was added, and the light pink precipitate was filtered off and washed, first with water and then with methanol. The solids were dried under vacuum at 40° C. to obtain 119 g. of crude 6-methoxy-2-(4-methoxyphenyl)-benzo[b]-thiophene. The crude product was slurried in hot methanol, filtered, and washed with cold methanol, and the solids were recrystallized from 4 liters of ethyl acetate, filtered, washed with hexane and dried to obtain 68 g. of purified intermediate product, m.p. 187°–190.5° C.

Ninety g. of pyridine hydrochloride was added to a flask equipped with a distillation head, condenser and collecting flask, and was heated with stirring until the temperature in the distillation head was 220° C. The distillation apparatus was then removed, the pot was cooled to 210° C., and 30 g. of the aboveprepared dimethoxy intermediate was added. The mixture was stirred at 210° C. for 30 minutes, and was then poured into 250 ml. of ice-water. The precipitate was extracted into 500 ml. of ethyl acetate, and the organic layer was washed with 150 ml. of saturated aqueous sodium bicarbonate and then with 150 ml. of saturated aqueous sodium chloride. The organic layer was then dried over magnesium sulfate, filtered and evaporated to dryness under vacuum to obtain 25.5 g. of the desired intermediate product, m.p. >260° C.

The next two examples illustrate acylations which produce compounds of this invention having acetyl and benzoyl R and $R^1$ groups, respectively.

EXAMPLE 1

6-acetoxy-2-(4-acetoxyphenyl)-3-[4-(2-piperidinoethoxy)benzoyl]benzo[b]thiophene, hydrochloride An acylating agent, in acid chloride form, was prepared by combining 26.3 g. of 4-(2-piperidinoethoxy)-benzoic acid, hydrochloride, 36.5 g. of thionyl chloride and 1 drop of dimethylformamide in 200 ml. of 1,2-dichloroethane, and stirring the mixture under reflux for 2 hours under a nitrogen atmosphere. The mixture was then evaporated to dryness under vacuum to obtain the desired 4-(2-piperidinoethoxy)benzoyl chloride, hydrochloride, which was dissolved in 1 liter of 1,2-dichloroethane. To the solution was added 20 g. of 6-acetoxy-2-(4-acetoxyphenyl)benzo[b]thiophene and the mixture was stirred vigorously. To it was then added, over about 3 minutes, 73.4 g. of aluminum chloride. During the addition, the reaction mixture turned dark brown and hydrogen chloride evolved. The mixture was then stirred for one hour, and was poured over 1 liter of ice-water. The layers were separated, and the aqueous layer was extracted three times with 200 ml. portions of warm chloroform. The organic layers were combined and dried over magnesium sulfate, and were then filtered and evaporated under vacuum to obtain a brownish-yellow oil, which are not purified. The presence of the desired product was confirmed by thin layer chromatography (TLC) on silica gel, eluting with 9/1 chloroform/methanol, which showed that the major constituent ran at the same $R_f$ as authentic 6-acetoxy-2l-(4-acetoxyphenyl)-3-[4-(2-piperidinoethoxy)benzoyl]-benzo[b]thiophene.

EXAMPLE 2

6-benzoyloxy-2-(4-benzoyloxyphenyl)-3-[4-(2-piperidinoethoxy)benzoyl]benzo[b]thiophene, hydrochloride The process of this example was run as was the process of Example 1, starting with the acid chloride formed from 18.9 g. of 4-(2-piperidinoethoxy)-benzoic acid, hydrochloride, and 20 g. of 6-benzoyloxy-2-(4-benzoyloxyphenyl)-benzo[b]thiophene. The reaction mixture was stirred for 1.5 hours, and was then worked up as described in Example 1 to obtain the desired product as an oil. A small portion of the crude product was crystallized from denatured ethanol to provide an analytical sample, m.p. 230°–233° C., the identity of which was confirmed by nmr analysis.

δ1.30–2.50 (6H, m, NH(CH$_2$CH$_2$)CH$_2$); 2.50–3.75 (6H, m, NH(CH$_2$CH$_2$)$_2$CH$_2$ and OCH$_2$CH$_2$N); 4.56 (2H, m, OCH$_2$CH$_2$N); 6.77 (2H, d, J=9 Hz, aromatic o to OCH$_2$); 7.10 (2H, d, J=9 Hz, aromatic o to OCO); 7.10–7.90 (17H, m, aromatic); 8.00–8.27 (6H, m, aromatic o to CO); 12.30–12.80 (1H, broad s, NH).

The next two preparations illustrate the acylation of sulfonyl-protected starting compounds.

Preparation 7

6-benzenesulfonyloxy-2-(4-benzenesulfonyloxyphenyl)-3-[4-(2-piperidinoethoxy)benzoyl]benzo-[b]thiophene, hydrochloride An acid chloride was formed from 8.21 g. of 4-(2-piperidinoethoxy)benzoic acid, hydrochloride, as described in Example 1, and was combined with 10 g. of 6-benzenesulfonyloxy-2-(4-benzenesulfonyloxyphenyl)-benzo[b]thiophene in 500 ml. of 1,2-dichloroethane and treated with 22.9 g. of aluminum chloride. The mixture was stirred at ambient temperature overnight, and worked up as described in Example 1 above. The product was 15 g. of tan foam which would not crystallize. A 1 g. sample of the crude product was purified by column chromatography over a 4×20 cm. silica gel column, eluting first with chloroform, and then with 25% methanol in chloroform. The product-containing fractions were combined, treated with hydrochloric acid to form the hydrochloride salt, and evaporated to dryness under vacuum to provide the product as an oil, the identity of which was confirmed by an absorption maximum at 1645 cm$^{-1}$ in its infrared spectrum, indicative of the —CO— function of the desired product. Its identity was further confirmed by its conversion to 6-hydroxy-2-(4-hydroxyphenyl)-3-[4-(2-piperidinoethoxy)benzoyl]-benzo[b]thiophene in Example 6 below.

Preparation 8

6-methanesulfonyloxy-2-(4-methanesulfonyloxyphenyl)-3-[4-(2-piperidinoethoxy)benzoyl]benzo[b]-thiophene, hydrochloride The acid chloride was formed from 2.0 g. of 4-(2-piperidinoethoxy)benzoic acid, hydrochloride, as described in Example 1, and was combined with 2 g. of 6-methanesulfonyloxy-2-(4-methanesulfonyloxyphenyl)-benzo[b]thiophene in 50 ml. of dichloromethane. A 2.4 g. portion of trifluoromethanesulfonic acid was added, and the mixture was stirred overnight under reflux. The reaction mixture was then poured over ice and sodium bicarbonate solution, and the organic layer was dried over magnesium sulfate and filtered. The filtrate was evaporated under vacuum to a yellow foam, which was treated with excess 3% hydrogen chloride in anhydrous methanol. The mixture was evaporated to dryness under vacuum to obtain a white foam which was dissolved in 18 ml. of boiling methanol. The solution was cooled to obtain 3.1 g. of the desired product, m.p. 128°–130° C., which was identified by nmr analysis.

δ1.50–2.00 (6H, m, N—(CH$_2$CH$_2$)$_2$CH$_2$); 2.57–3.75 (6H, m, NH(CH$_2$CH$_2$)$_2$CH$_2$ and OCH$_2$CH$_2$N); 3.36 (3H, s, CH$_3$SO$_2$); 3.46 (3H, s, CH$_3$SO$_2$); 4.45 (2H, broad t, J=6 Hz, OCH$_2$CH$_2$N); 6.97 (2H, d, J=9 Hz, aromatic o to OCH$_2$); 7.25–7.80 (8H, m, aromatic); 8.25 (1H, d, J=2 Hz, aromatic, o to O and S); 10.70–11.00 (1H, broad s, NH). Infrared absorption in KBr for the ketone CO appears at 1640 cm.$^{-1}$. Ultraviolet absorption maxima: $\lambda_{max}$ ($\epsilon$) in ethanol: 273 nm. (sh 26,000), 290 (29,500).

The next two preparations demonstrate the synthesis of intermediates which have leaving groups on the side chains.

Preparation 9

6-methanesulfonyloxy-2-(4-methanesulfonyloxyphenyl)-3-[4-(2-chloroethoxy)benzoyl]benzo[b]thiophene The acid chloride was prepared from 1.1 g. of 4-(2-chloroethoxy)benzoic acid as described in Example 1, and the acid chloride was combined with 1.2 g. of 6-methanesulfonyloxy-2-(4-methanesulfonyloxyphenyl)-benzo[b]thiophene in 25 ml. of 1,2-dichloroethane in the presence of 0.5 ml. of trifluoromethanesulfonic acid. The mixture was stirred under reflux for 2 hours and was then poured into ice-water. The organic layer was separated, extracted with sodium bicarbonate solution, dried over magnesium sulfate and concentrated under vacuum to obtain 1.9 g. of impure product. Chromatography over a 4×8 cm. silica gel column, eluting with 9/1 toluene/ethyl acetate gave 1.2 g. of impure intermediate product, which was recrystallized from methanol to provide white crystals, m.p. 123°–124° C. The absorption maximum for the CO function appeared at 1650 cm.$^{-1}$ in the infrared spectrum taken in chloroform.

Preparation 10

6-methanesulfonyloxy-2-(4-methanesulfonyloxyphenyl)-3-[4-(2-bromoethoxy)benzoyl]benzo[b]thiophene One g. of 4-(2-bromoethoxy)benzoic acid was converted to the acid chloride, and was combined with 1.2 g. of 6-methanesulfonyloxy-2-(4-methanesulfonyloxyphenyl)benzo[b]thiophene, 20 ml. of dichloromethane and 0.5 ml. of trifluoromethanesulfonic acid. The mixture was stirred under reflux overnight, and was then poured into ice-water. The organic layer was separated, washed with sodium carbonate solution, dried and evaporated under vacuum to obtain 2.1 g. of brown oil. The oil was chromatographed over a 4×8 cm. silica gel column with 9/1 toluene/ethyl acetate and the product-containing fractions were combined and evaporated under vacuum to obtain 1.8 g. of purified product as an oil. The product was identified by its MH$^+$ molecular ion, m/e 626, in the field desorption mass spectrum and by an absorption maximum in the infrared spectrum, in chloroform, at 1645 cm.$^{-1}$ attributable to the CO function. A small sample was recrystallized from methanol to obtain white crystals, m.p. 105°–107° C.

The following two preparations illustrate the displacement of side chain leaving groups with piperidine.

Preparation 11

6-methanesulfonyloxy-2-(4-methanesulfonyloxyphenyl)-3-[4-(2-piperidinoethoxy)benzoyl]benzo[b]-thiophene, hydrochloride A 1.5 g. portion of 6-methanesulfonyloxy-2-(4-methanesulfonyloxyphenyl)-3-[4-(2-bromoethoxy)benzoyl]benzo[b]thiophene was combined with 5 ml. of piperidine, 25 ml. of anhydrous dimethylformamide and 150 mg. of potassium iodide. The mixture was stirred at ambient temperature for two hours, and was then evaporated to dryness under vacuum. To the residue was added 25 ml. of saturated aqueous sodium bicarbonate and the mixture was extracted with two 25 ml. portions of ethyl acetate. The organic layers were combined and washed five times with 20 ml. portions of aqueous sodium chloride, dried over magnesium sulfate and evaporated under vacuum to a brown oil. To the oil was added 50 ml. of 3% hydrogen chloride in methanol, and the mixture was evaporated to dryness again. To it was added 10 ml. of methanol, and the mixture was warmed and evaporated down to about 8 ml. It was then cooled, and the purified intermediate product, m.p. 128°–130° C., precipitated. About 1.6 g. of purified intermediate product was obtained.

Preparation 12

6-methanesulfonyloxy-2-(4-methanesulfonyloxyphenyl)-3-[4-(2-piperidinoethoxy)benzoyl]benzo[b]thiophene, hydrochloride An 0.58 g. portion of 6-methanesulfonyloxy-2-(4-methanesulfonyloxyphenyl)-3-[4-(2-chloroethoxy)-benzoyl]benzo[b]thiophene was combined with 20 ml. of dimethylformamide, 4.8 ml. of piperidine and 100 mg. of potassium iodide, and the mixture was stirred overnight at 40° C. and then at 50° C. for two hours. The mixture was evaporated to a brown oil under vacuum, and the oil was worked up by pouring it into 50 ml. of saturated aqueous sodium bicarbonate and extracting the mixture twice with 40 ml. portions of ethyl acetate. The organic layers were combined, washed twice with 100 ml. portions of saturated aqueous sodium chloride and concentrated under vacuum to an oil. To the oily residue was added 50 ml. of 3% hydrogen chloride in methanol, and the acidic mixture was concentrated again to an oil, which was dissolved in hot denatured ethanol and crystallized. The first crop of purified crystals amounted to 0.4 g. and had a melting point and infrared and ultraviolet spectra identical to those of the products of Preparations 8 and 11.

The next four examples illustrate the preparation of dihydroxy compounds of this invention by the hydrolysis of the protected compounds which have been prepared above.

EXAMPLE 3

6-hydroxy-2-(4-hydroxyphenyl)-3-[4-(2-piperidinoethoxy)benzoyl]benzo[b]thiophene A 4 g. portion of 6-methanesulfonyloxy-2-(4-methanesulfonyloxyphenyl)-3-[4-(2-piperidinoethoxy)-benzoyl]benzo[b]thiophene, hydrochloride, was combined with 100 ml. of denatured alcohol and 10 ml. of 5 N sodium hydroxide, and stirred under reflux for 1.5 hours under a nitrogen atmosphere. The reaction mixture was then evaporated to dryness under vacuum, and the residue was dissolved in 200 ml. of water and washed with 300 ml. of diethyl ether. The water layer was degassed under vacuum, and then nitrogen was bubbled through it to remove all traces of ether. The mixture was then acidified with 1 N hydrochloric acid, and then made basic with excess sodium bicarbonate. The precipitate was collected by filtration and washed with cold water to obtain 2.4 g. of crude product. It was purified on a 2×30 cm. column of silica gel, eluting first with 700 ml. of 5% methanol in chloroform, followed by 1 liter of 10% methanol in chloroform. The impurities came off first, and the product-containing fractions were combined and evaporated under vacuum to obtain 1.78 g. of yellow oil. The oil was dissolved in 6 ml. of acetone, seeded and chilled in a freezer to obtain 1.2 g. of purified product, m.p. 143°–147° C. The identity of the product was confirmed as follows:

nmr spectrum (100 mHz in dmso-$d_6$) δ1.20–1.65 (6H, m, N(CH$_2$C$\underline{H}_2$)$_2$C$\underline{H}_2$); 2.30–2.45 (4H, m, N(C$\underline{H}_2$CH$_2$)$_2$CH$_2$); 2.60 (2H, t, J=6 Hz, OCH$_2$C$\underline{H}_2$N); 4.06 (2H, t, J=6 Hz, OC$\underline{H}_2$CH$_2$N); 6.68 (2H, d, J=9H, aromatic o to OH); 6.85 (1H, q, $J_{H4-H5}$=9 Hz, $J_{H5-H7}$=2 Hz, H5 of benzothiophene ring); 6.90 (2H, d, J=9 Hz, aromatic o to OCH$_2$CH$_2$N); 7.18 (2H, d, J=9 Hz, aromatic m to OH); 7.25 (1H, d, J=9 Hz, H4 of benzothiophene ring); 7.66 (2H, d, J=9 Hz, aromatic o to CO); 9.72 (2H, broad s, OH). Ultraviolet spectrum in ethanol: $\lambda_{max}$ (ε): 290 nm. (34,000). Electron impact mass spectrum M+ at m/e 473.

EXAMPLE 3A 6-hydroxy-2-(4-hydroxyphenyl)-3-[4-(2-piperidinoethoxy)benzoyl]benzo[b]thiophene A 3.6 g. portion of 6-methanesulfonyloxy-2-(4-methanesulfonyloxyphenyl)-3-[4-(2-piperidinoethoxy)-benzoyl]benzo[b]thiophene was dissolved in 100 ml. of tetrahydrofuran and 40 ml. of methanol, and 10 ml. of 5 N sodium hydroxide was added. The mixture was stirred for 16 hours at ambient temperature, and was then worked up by the procedure of Example 3 above to obtain 3.5 g. of a yellow solid. The impure product was purified by column chromatography on silica gel, eluting with a gradient solvent from 5% methanol in chloroform to 30% methanol in chloroform. The product-containing fractions were evaporated to obtain 1.85 g. of oily product, which was recrystallized from acetone to obtain 1.25 g. of purified product, m.p. 141°–144° C.

EXAMPLE 4

6-hydroxy-2-(4-hydroxyphenyl)-3-[4-(2-piperidinoethoxy)benzoyl]benzo[b]thiophene The oily product of Example 1 above, 6-acetoxy-2-(4-acetoxyphenyl)-3-[4-(2-piperidinoethoxy)benzoyl]benzo[b]thiophene, hydrochloride, was dissolved in 700 ml. of methanol and 100 ml. of 5 N sodium hydroxide. The mixture was stirred at ambient temperature for two hours, and was then evaporated to an oil under vacuum at a temperature below 40° C. The residue was dissolved in 500 ml. of water and washed twice with 500 ml. portions of diethyl ether. The aqueous layer was acidified to pH 2 with cold 50% aqueous methanesulfonic acid, diluted to about 3 liters, and washed twice with 1 liter portions of diethyl ether. The aqueous layer was then separated, thoroughly degassed under vacuum, and made basic with aqueous ammonia. The resulting solids were collected by filtration and vacuum dried at 40° C. to obtain 14.2 g. of crude product which was chromatographed over a 5×5 cm. column of Activity I silica gel, eluting with 15% methanol in chloroform. The product-containing fractions were evaporated to dryness to obtain a yellow foam, which was recrystallized from acetone to obtain 11.9 g. of product, which was substantially identical to the product of Example 3 above by nmr, ultraviolet and infrared analysis.

EXAMPLE 5

6-hydroxy-2-(4-hyroxyphenyl)-3-[4-(2-piperidinoethoxy)benzoyl]benzo[b]thiophene

The crude product of Example 2 above, 6-benzoyloxy-2-(4-benzoyloxyphenyl)-3-[4-(2-piperidinoethoxy)benzoyl]benzo[b]thiophene, hydrochloride, was combined with 400 ml. of ethanol, 400 ml. of water and 55 ml. of methanesulfonic acid. The mixture was stirred on the steam bath for 72 hours, and was then evaporated down to an oil which was diluted to about 6 liters with water. The aqueous solution was washed twice with 1 liter portions of diethyl ether, and was then thoroughly degassed under vacuum, cooled to about 20° C., and made basic with aqueous ammonia to pH 8.4. The product which precipitated was collected by filtration and vacuum dried, and was then recrystallized from about 80 ml. of acetone. The product was vacuum dried at 40° C. to obtain 18.1 g. of crystals which was found by nmr, mass spectrum, infrared and ultraviolet analysis to be substantially identical to the product of Example 3.

EXAMPLE 6

6-hydroxy-2-(4-hydroxyphenyl)-3-[4-(2-piperidinoethoxy)benzoyl]benzo[b]thiophene The oily 6-benzenesulfonyloxy-2-(4-benzenesulfonyloxyphenyl)-3-[4-(2-piperidinoethoxy)benzoyl]-benzo[b]thiophene, hyrochloride, which was prepared in Preparation 6 above was added to 300 ml. of denatured ethanol and 30 ml. of 5 N sodium hyroxide under a nitrogen atmosphere, and stirred under reflux for two hours. The mixture was then evaporated under vacuum, and the residue was dissolved in 600 ml. of water, which was washed with 800 ml. of diethyl ether. The aqueous layer was made acid to pH 2.0 with methanesulfonic acid, diluted to 6 liters with additional water, and washed twice with 2-liter portions of diethyl ether. The aqueous layer was degassed under vacuum, and made basic to pH 8.4 with aqueous ammonia. The resulting yellow-brown crystals were collected, washed with water and vacuum dried at 40° C., to obtain 7.4 g. of the expected product. A final recrystallization of the product from acetone provided light tan crystals which by nmr, infrared, and ultraviolet spectra were substantially identical to the desired product prepared in Example 3 above.

The next example illustrates a synthesis of the dihydroxy compound of this invention from an intermediate having a leaving group on the side chain by displacement of the leaving group with piperidine and cleavage of the protecting groups in a single step.

EXAMPLE 7

6-hydroxy-2-(4-hydroxyphenyl)-3-[4-(2-piperidinoethoxy)benzoyl]benzo[b]thiophene A 1.5 g. portion of 6-methanesulfonyloxy-2-(4-methanesulfonyloxyphenyl)-3-(4-bromoethoxybenzoyl)-benzo[b]thiophene, hydrochloride, was combined with 25 ml. of dimethylformamide, 5 ml. of piperidine and 150 mg. of potassium iodide, and was stirred for two hours at ambient temperature. The reaction was then heated to 110° C. in an oil bath, under a nitrogen atmosphere, and stirred for 5 days. The course of the reaction was followed by thin layer chromatography on silica gel plates, using a 9/1 mixture of chloroform/methanol as the eluting solvent. As the reaction went on, the spot indicating the protected compound gradually disappeared, and was replaced, first by spots indicating the two possible mono-protected compounds, and then by a spot indicative of the desired product.

EXAMPLE 8

6-hydroxy-2-(4-hydroxyphenyl)-3-[4-(2-piperidinoethoxy)benzoyl]benzo[b]thiophene, hydrochloride Under a nitrogen blanket, a mixture of 3 g. of 4-(2-piperidinoethoxy)benzoic acid, hydrochloride, 2 drops of dimethylformamide, 2.5 ml. of thionyl chloride and 40 ml. of chlorobenzene was heated at 70°–75° C. for about one hour. The excess thionyl chloride and 15–20 ml. of solvent were then distilled off. The remaining suspension was cooled to ambient temperature, and to it were added 100 ml. of dichloromethane, 2.7 g. of 6-methoxy-2-(4-methoxyphenyl)benzo[b]thiophene and 10 g. of aluminum chloride. The solution was stirred for about one hour, 7.5 ml. of ethanethiol was added, and the mixture was stirred for 45 minutes more. Then 40 ml. of tetrahydrofuran was added, followed by 15 ml. of 20% hydrochloric acid, with an exotherm to reflux. Fifty ml. of water and 25 ml. of saturated aqueous sodium chloride was added. The mixture was stirred and allowed to cool to ambient temperature. The precipitate was collected by filtration and washed successively with 30 ml. of water, 40 ml. of 25% aqueous tetrahydrofuran, and 35 ml. of water. The solids were then dried at 40° C. under vacuum to obtain 5.05 g. of product, which was identified by nmr.

$\delta$1.7 (6H, m, N(CH$_2$C$\underline{H}_2$)$_2$C$\underline{H}_2$); 2.6–3.1 (2H, m, NCH$_2$); 3.5–4.1 (4H, m, NCH$_2$); 4.4 (2H, m, OCH$_2$); 6.6–7.4 (9H, m, aromatic); 7.7 (2H, d, aromatic o to CO); 9.8 (2H, m, OH).

The following group of examples illustrates the preparation of ester derivatives of this invention from the dihydroxy compound.

EXAMPLE 9

6-trifluoroacetoxy-2-(4-trifluoroacetoxyphenyl)-3-[4-(2-piperidinoethoxy)benzoyl]benzo[b]thiophene, trifluoroacetate One g. of 6-hydroxy-2-(4-hydroxyphenyl)-3-[4-(2-piperidinoethoxy)benzoyl]benzo[b]thiophene was dissolved in 10 ml. of tetrahydrofuran and combined with 0.25 ml. of trifluoroacetic acid and 1 ml. of trifluoroacetic anhyride. The mixture was stirred for 5 minutes, and then was evaporated to a pale green oil under vacuum at 40° C. A field desorption high resolution mass spectrum showed m/e 665.128, correct for the desired diester. An infrared spectrum in deuterochloroform showed a strong absorption at 1800 cm.$^{-1}$ attributable to the CF$_3$CO$_2$ carbonyl in addition to the ketone carbonyl absorption at 1650 cm.$^{-1}$.

Further observation of the product after several days indicated that some hydrolysis of one or both ester groups had occurred.

EXAMPLE 10

6-acetoxy-2-(4-acetoxyphenyl)-3-[4-(2-piperidinoethoxy)benzoyl]benzo[b]thiophene Two g. of 6-hydroxy-2-(4-hydroxyphenyl)-3-[4-(2-piperidinoethoxy)benzoyl]benzo[b]thiophene was dissolved in 30 ml. of tetrahydrofuran, and 3.5 g. of potassium carbonate was added. The vessel was blanketed with nitrogen and 0.9 g. of acetic anhydride was added. The mixture was stirred at ambient temperature for 2 hours, and then under reflux for 2 hours more. The mixture was then cooled, and to it was added 200 ml. of chloroform. The mixture was washed with 100 ml. of aqueous sodium chloride solution, and the organic layer was dried over magnesium sulfate, filtered and evaporated to dryness under vacuum at 40° C. A white foam was obtained, which was determined to be the desired product.

nmr spectrum: $\delta$1.50 (6H, m, N(CH$_2$C$\underline{H}_2$)$_2$CH$_2$); 2.24 (3H, s, CH$_3$CO); 2.32 (3H, s, CH$_3$CO); 2.46 (4H, broad t, J=5 Hz, N(C$\underline{H}_2$CH$_2$)$_2$CH$_2$); 2.72 (2H, t, J=7 Hz, OCH$_2$C$\underline{H}_2$N); 4.06 (2H, t, J=7 Hz, OC$\underline{H}_2$CH$_2$N); 6.74 (2H, d, J=9 Hz, aromatic o to OCH$_2$); 6.95 (2H, d, J=9 Hz, aromatic o to OCOCH$_3$); 7.05 (1H, q, J$_{H4-H5}$=9 Hz and J$_{H5-H7}$=2 Hz, H5 of the benzothiophene ring); 7.42 (2H, d, J=9 Hz, aromatic m to OCOCH$_3$); 7.70 (2H, d, J=9 Hz, aromatic o to CO). The signals for H4 and H7 of the benzothiophene ring were somewhat obscured by other peaks, but appeared between $\delta$7.75 and 7.80. The infrared spectrum in chloroform showed a strong maximum at 1760 cm.$^{-1}$, attributable to the acetate ester groups. The high resolution mass spectrum showed m/e 557.186.

EXAMPLE 11

6-dodecanoyloxy-2-(4-dodecanoyloxyphenyl)3-[4-(2-piperidinoethoxy)benzoyl]benzo[b]thiophene The process of this example was carried out as described above in Example 10, using 1.9 g. of lauroyl chloride as the acylating agent. The evaporation of the washed reaction mixture gave an oil, which was purified by chromatography over a 2 inch $\times$ 3 inch silica gel column eluted with 19/1 chloroform/methanol. The product-containing fractions were combined and concentrated under vacuum at 40° C. for 12 hours to obtain an oily solid, which was confirmed to be the desired product by a strong absorption at 1750 cm.$^{-1}$ on the infrared spectrum in chloroform, attributable to the ester carbonyl groups. The field desorption mass spectrum showed the correct molecular ion, m/e 837.494, for the desired product. The nmr spectrum was poorly resolved.

EXAMPLE 12

6-ethoxycarbonyloxy-2-(4-ethoxycarbonyloxyphenyl)-3-[4-(2-piperidinoethoxy)benzoyl]benzo[b]thiophene The process of this reaction was carried out as described above in Example 10, using 1.0 g. of ethyl chloroformate as the acylating agent. The evaporation of the washed reaction mixture provided a pale green oil, which was confirmed to be the desired product by the carbonyl absorption at 1762 cm.$^{-1}$ in the infrared spectrum in chloroform. The high resolution mass spectrum showed m/e 617.207. The nmr spectrum was consistent with the structure.

$\delta$1.36 (3H, t, J=7 Hz, CH$_2$C$\underline{H}_3$); 1.41 (3H, t, J=7 Hz, CH$_2$C$\underline{H}_3$); 1.63 (6H, m, N(CH$_2$C$\underline{H}_2$)$_2$C$\underline{H}_2$); 2.61 (4H, m, N(C$\underline{H}_2$CH$_2$)$_2$CH$_2$); 2.85 (2H, t, J=7 Hz, OCH$_2$C$\underline{H}_2$N); 4.17 (2H, t, J=7 Hz, OC$\underline{H}_2$CH$_2$N); 4.28 (2H, q, J=7 Hz, OC$\underline{H}_2$CH$_3$); 4.34 (2H, q, J=7 Hz, OC$\underline{H}_2$CH$_3$); 6.75 (2H, d, J=9 Hz, aromatic o to OCH$_2$CH$_2$N); 7.05 (2H, d, J=9 Hz, aromatic o to OCO$_2$C$_2$H$_5$); 7.15 (1H, q, J=9 Hz, J=2 Hz, H5 of benzothiophene ring); 7.44 (2H, d, J=9 Hz, aromatic m to OCO$_2$C$_2$H$_5$); 7.63 (1H, d, J=9 Hz, H4 of benzothiophene ring); 7.72 (2H, d, J=9 Hz, aromatic o to CO); 7.73 (1H, d, J=2 Hz, H7 of benzothiophene ring).

EXAMPLE 13

6-benzoyloxy-2-(4-benzoyloxyphenyl)-3-[4-(2-piperidinoethoxy)benzoyl]benzo[b]thiophene, hydrochloride A 2 g. portion of 6-hydroxy-2-(4-hydroxyphenyl)-3-[4-(2-piperidinoethoxy)benzoyl]benzo[b]-thiophene was suspended in 35 ml. of chloroform, and 3.5 g. of potassium carbonate was added. The flask was blanketed with nitrogen, and 2 mg. of 4-dimethylaminopyridine and 1.2 g. of benzoyl chloride were added. The mixture was heated in an 80° C. oil bath for 4 hours under reflux, and was then poured into a large amount of aqueous sodium chloride solution. The mixture was then extracted three times with 50 ml. portions of chloroform, and the organic layers were combined and washed with aqueous sodium chloride solution and dried over magnesium sulfate. The solution was then filtered, and hydrogen chloride gas was bubbled through it. Solvent was then removed under vacuum, leaving a gray oil, which was triturated with denatured alcohol and seeded with an authentic sample of the desired product to obtain white crystals, which were washed with diethyl ether and recrystallized from dichloromethane/ethanol to obtain 1.86 g. of the desired product, m.p. 235°–236° C.

EXAMPLE 14

6-methoxy-2-(4-methoxyphenyl)-3-[4-(2-piperidinoethoxy)benzoyl]benzo[b]thiophene, hydrochloride A 3 g. portion of 4-(2-piperidinoethoxy)-benzoic acid, hydrochloride, was combined with 20 ml. of 1,2-dichloroethane and 2 drops of dimethylformamide at −20° C., and 4 ml. of phosgene was added. The mixture was stirred for 90 minutes while the temperature was slowly raised to reflux, and then for 30 minutes at reflux. An additional 80 ml. of 1,2-dichloroethane was added, and then 2.7 g. of 6-methoxy-2-(4-methoxyphenyl)benzo[b]thiophene. An 8.68 g. portion of aluminum chloride was added, and the mixture was stirred for 3 hours. An additional 2.66 g. of aluminum chloride was added, and the mixture was stirred for 16 hours more. The mixture was poured into a large amount of 1/1 dichloromethane/dilute aqueous hydrochloric acid. Additional dichloromethane containing a little methanol was added until distinct layers separated. The water layer was extracted several times with dichloromethane containing a little methanol, and the organic layers were combined and washed with water and with aqueous sodium chloride. The organic layer was then filtered and evaporated to an oil, which was dissolved in dichloromethane and a little methanol, and extracted with about 20 ml. of 5% aqueous sodium hydroxide, and then with water, aqueous ammonium chloride and water. The organic layer was then evaporated to about 4 g. of oil, which was dissolved in acetone. Diethyl ether was added, and impurities precipitated and were filtered out. The filtrate was evaporated to about 3.4 g. of foam, which was purified by preparative high-pressure liquid phase chromatography on silica gel, eluting with 1.5% methanol in chloroform. The product-containing fractions were combined and evaporated to obtain the desired product as 1.88 g. of yellow oil; m/e 501.198 by electron impact high resolution mass spectrometry; absorption maximum at 1650 on the infrared spectrum in chloroform; $\lambda_{max}$ ($\epsilon$): 296 (32,500) on the ultraviolet spectrum in ethanol.

The following example shows a preferred synthesis of a preferred salt.

EXAMPLE 15

6-hydroxy-2-(4-hydroxyphenyl)-3-[4-(2-piperidinoethoxy)benzoyl]benzo[b]thiophene, hydrochloride Five hundred mg. of the product of Example 3 was dissolved in 20 ml. of tetrahydrofuran, and the solution was dried over 4A molecular sieves. Hydrogen chloride gas was then bubbled through the solution, and a pale yellow solid precipitated. The solid product was collected by filtration, washed with diethyl ether and vacuum dried at ambient temperature to obtain 524 mg. of the desired product, m.p. 221°–224° C. The ultraviolet spectrum in ethanol showed $\lambda_{max}$ ($\epsilon$) 222 nm. (29,000), 287 nm. (28,000).

nmr (100 mHz, dmso-d$_6$): δ1.76 (6H, m, N(CH$_2$CH$_2$)$_2$CH$_2$); 3.40 (6H, m, N(CH$_2$CH$_2$)$_2$CH$_2$ and OCH$_2$CH$_2$N); 4.42 (2H, m, OCH$_2$CH$_2$N); 6.66 (2H, d, J=9 Hz, aromatic o to OH); 6.85 (1H, q, J=9 Hz and J=2 Hz, H5 of benzothiophene ring); 6.95 (2H, d, J=9 Hz, aromatic o to OCH$_2$CH$_2$N); 7.15 (2H, d, J=9 Hz, aromatic m to OH); 7.23 (1H, d, J=9 Hz, H4 of benzothiophene ring); 7.34 (1H, d, J=2 Hz, H7 of benzothiophene ring); 7.68 (2H, d, J=9 Hz, aromatic o to CO); 9.76 (2H, broad s, OH); 10.40 (1H, broad s, NH).

EXAMPLE 16

6-hydroxy-2-(4-hydroxyphenyl)-3-[4-(2-piperidinoethoxy)benzoyl]benzo[b]thiophene, hydrochloride A mixture of 1.5 g. of 4-(2-piperidinoethoxy)-benzoic acid, hydrochloride, 20 ml. of chlorobenzene, 3 ml. of thionyl chloride and 2 drops of dimethylformamide was stirred at 75°–79° for 2 hours, to prepare the corresponding acid chloride. Vacuum was then applied, and the temperature dropped to 65°. Distillation was continued until the pot temperature was 90°. Twenty ml. of additional chlorobenzene was added, and the mixture was redistilled to a pot temperature of 90°, and was then cooled. To the mixture was added 15 ml. of dichloromethane, 1.35 g. of 6-methoxy-2-(4-methoxyphenyl)-benzo[b]thiophene, 5 g. of aluminum chloride and 15 ml. of additional dichloromethane. The mixture was stirred at 27°–29° for 90 minutes, and then 1.6 ml. of ethanethiol was added. The mixture was stirred with cooling to maintain it at or below 35°. After 30 minutes, the mixture was worked up as described in Example 8 above, except that only 18 ml. of tetrahydrofuran and of water were used, to obtain 2.6 g. of the crude desired product, m.p. 217°, which was found to be substantially identical to the product of Example 8 by nmr and thin layer chromatography.

EXAMPLE 17

6-hydroxy-2-(4-hydroxyphenyl)-3-[4-(2-piperidinoethoxy)benzoyl]benzo[b]thiophene, hydrochloride The process of Example 16 was followed once more, except that 1.8 ml. of ethanethiol was used, and a different work up procedure was applied as follows. The mixture was stirred for 30 minutes after the addition of the ethanethiol, and to it was added 4 ml. of methanol, producing vigorous evolution of gas and a temperature rise, with cooling, to 30° C. Six ml. more methanol was added, followed by 5 ml. of 20% hydrochloric acid and 18 ml. of water, while the mixture was held at about 25° C. The mixture was stirred for about 30 minutes, and was then filtered. The solids were washed twice with 25 ml. portions of water and twice with 25 ml. portions of diethyl ether. The solids were dried, and found to be 2.55 g. of the crude desired product, m.p. 219° C. dec., essentially identical to the product of Example 8 by nmr and thin layer chromatography.

EXAMPLE 18

Purification of 6-hydroxy-2-(4-hydroxyphenyl)-3-[4-(2-piperidinoethoxy)benzoyl]benzo[b]thiophene, hydrochloride Two hundred g. of crude 6-hydroxy-2-(4-hydroxyphenyl)-3-[4-(2-piperidinoethoxy)benzoyl]benzo[b]thiophene, hydrochloride, typical of the product of Example 16 above, was added to 4400 ml. of methanol and 60 ml. of deionized water in a 5-liter flask. The slurry was heated to reflux, whereupon most of the crude product went into solution. The remaining solid was removed by filtration under vacuum, using a filter aid pad. A distillation head was then attached to the flask, and solvent was distilled off until the volume of the remaining solution was about 1800 ml. The heating mantle was then turned off, and the solution was cooled very slowly overnight, with constant stirring. The crystalline product was then collected by vacuum filtration, and the flask was washed out with filtrate to obtain all of the product. The crystals were washed on the filter with two 100 ml. portions of cold (below 0° C.) methanol, and the washed product was dried at 60° C. under vacuum to obtain 140 g. of dried product.

The product was slurried in 3000 ml. of methanol and 42 ml. of water, heated to reflux and cooled very slowly. The product was filtered and dried as above to obtain 121 g. of highly purified product, m.p. 259°–260° C.

EXAMPLE 19

6-Methoxy-2-(4-hydroxyphenyl)-3-[4-(2-piperidinoethoxy)benzoyl]benzo[b]thiophene, hydrochloride A mixture of 9 g. of 4-(2-piperidinoethoxy)benzoic acid, hydrochloride, 100 ml. of chlorobenzene, 15 ml. of thionyl chloride and 5 drops of dimethylformamide was stirred at 75°–79° C. for 2 hours, to prepare the corresponding acid chloride. Excess thionyl chloride and part of the chlorobenzene was removed by distillation under vacuum to a maximum pot temperature of 85° C. Fifty ml. of additional chlorobenzene was added, and the distillation of 85° C. was repeated. The residue was then dissolved in 100 ml. of dichloromethane, and to it was added 8.1 g. of 6-methoxy-2-(4-methoxyphenyl)-benzo[b]thiophene, 50 ml. of additional dichloromethane and 30 g. of aluminum chloride. The mixture ws stirred at 27°–29° C. for 90 minutes, and was then cooled. To the mixture was added 108 ml. of tetrahydrofuran, followed by 30 ml. of 20% aqueous hydrochloric acid and 108 ml. of water. The water phase was then removed, and was extracted with 50 ml. of dichloromethane. The organic layers were combined, and extracted with 90 ml. of water. The organic portion was then dried over sodium sulfate, and evaporated to a solid under vacuum. About 31 g. of wet crude product was obtained.

The crude product was slurried in 200 ml. of hot chlorobenzene, and the slurry was cooled in an ice bath and filtered at 5° C. The solids were washed with 30 ml. of chlorobenzene, and dried under vacuum to obtain 10.6 g. of the desired product. About 1.8 g. of additional product was obtained by chromatography of the filtrate on silica gel, eluting with methanol. The melting point of the main product was 216° C. dec. Its identity was confirmed by 90 mHz nmr in CDCl$_3$, which showed the following characteristic features.

δ1.6 (m, 2H, N(CH$_2$CH$_2$)$_2$CH$_2$); 2.0 (m, 4H, N(CH$_2$CH$_2$)$_2$); 3.1 (m, 4H, N(CH$_2$CH$_2$)$_2$); 3.3 (m, 2H, CH$_2$N(CH$_2$)$_5$); 3.7 and 3.9 (s, 3H, OCH$_3$); 4.5 (n, 2H, OCH$_2$) 6.7–7.8 (m, 11H, aromatic).

The following reports of biological tests illustrate the usefulness of the compounds of this invention. The compound used in many of the tests reported below was the dihydroxy compound, 6-hydroxy-2-(4-hydroxyphenyl)-3-[4-(2-piperidinoethoxy)benzoyl]-benzo[b]thiophene.

The first test reported below is used to determine the estrogenic potency of compounds. It is well known that many compounds having antiestrogenic activity also, typically, have estrogenic activity. As has been explained, estrogenic activity is a liability in an antiestrogen, and thus it is important to identify antiestrogens having a minimum amount of estrogenic activity.

Test 1

Estrogenic Response Test

This test was conducted with immature 40–45 g. female rats, immature 11–13 g. mice, and adult ovariectomized mice. The rats were tested in groups of six, and mice in groups of ten. All of the laboratory animals were from standardized strains and were equilibrated to the laboratory before the test started. Each test was begun by administering the test compound daily for three days, as a subcutaneous injection or by oral gavage, as indicated below in the reports of individual experiments. Untreated control animals were included in each experiment, along with animals to which estradiol was administered subcutaneously. The estradiol-treated animals provided positive controls, showing the physiological effect of a potent estrogen on the individual group of animals used in the experiment. The usual dose of estradiol was 0.1 mcg./day, which dose approximates the physiological level.

The test animals were treated for three days and sacrificed on the fourth day, and the uteri were removed, freed of extraneous tissue, and blotted with paper towels. The uteri were weighed to the nearest 0.1 mg.

The tables below report the results of representative experiments. The doses of estradiol and of the compound of this invention are given as the total of the three daily doses. The uterine weights are given, in mg., as the means of all of the organ weights of the animals in a group. Compounds are referred to by their example numbers above.

TABLE I

| Treatment | Uterine Weight |
|---|---|
| Immature rats | |
| Experiment A | |
| Control | 23.0 mg. |
| Estradiol, 0.3 mcg., s.c. | 74.6 |
| Example 3, 3 mcg., s.c. | 47.7 |
| Example 3, 30 mcg., s.c. | 38.4 |
| Example 3, 300 mcg., s.c. | 35.9 |
| Example 3, 3 mg., s.c. | 33.9 |
| Experiment B | |
| Control | 23.8 mg. |
| Estradiol, 0.3 mcg., s.c. | 56.8 |
| Example 3, 3 mcg., oral | 34.5 |
| Example 3, 30 mcg., oral | 34.4 |

TABLE I-continued

| Treatment | Uterine Weight |
|---|---|
| Example 3, 300 mcg., oral | 33.2 |
| Example 3, 3 mcg., oral | 34.4 |
| Experiment C | |
| Control | 25.4 mg. |
| Estradiol, 0.3 mcg., s.c. | 63.1 |
| Example 9, 3 mg., s.c. | 31.3 |
| Example 10, 3 mg., s.c. | 30.8 |
| Example 11, 3 mg., s.c. | 37.1 |
| Example 12, 3 mg., s.c. | 35.8 |
| Example 13, 3 mg., s.c. | 39.6 |
| Example 14, 3 mg., s.c. | 35.1 |
| *Immature mice* | |
| Experiment D | |
| Control | 10.6 mg. |
| Estradiol, 0.03 mcg., s.c. | 33.3 |
| Estradiol, 0.09 mcg., s.c. | 48.2 |
| Estradiol, 0.3 mcg., s.c. | 50.3 |
| Example 3, 0.03 mcg., s.c. | 19.0 |
| Example 3, 0.3 mcg., s.c. | 19.3 |
| Example 3, 3 mcg., s.c. | 22.9 |
| Example 3, 30 mcg., s.c. | 23.9 |
| Example 3, 300 mcg., s.c. | 19.3 |
| Example 3, 3 mg., s.c. | 14.6 |
| *Mature ovariectomized mice* | |
| Experiment E | |
| Control | 12.3 mg. |
| Estradiol, 0.03 mcg., s.c. | 25.8 |
| Estradiol, 0.1 mcg., s.c. | 44.2 |
| Estradiol, 0.3 mcg., s.c. | 65.9 |
| Example 3, 0.3 mcg., s.c. | 18.2 |
| Example 3, 3 mcg., s.c. | 25.6 |
| Example 3, 30 mcg., s.c. | 26.2 |
| Example 3, 300 mcg., s.c. | 24.8 |
| Example 3, 3 mg., s.c. | 23.1 |

The experiments reported next below are antiestrogenic response experiments, in which the test animals were treated both with estradiol and with the same compound of this invention used in the experiments above. The purpose of the experiments below was to determine the extent to which the estrogenic response of estradiol could be inhibited by treatment with compounds of this invention.

Test 2

Antiestrogenic Tests

The same standardized types of laboratory animals which were used in the experiments described above were also used in these experiments. A compound of this invention, identified below by its example number, was administered, orally or subcutaneously, together with subcutaneous estradiol. Untreated control animals were used in each experiment. The dose of estradiol in each experiment is given in the first line of each table, followed by the doses of the compound of this invention which were given along with the established dose of estradiol to produce inhibition of the estrogenic effect of the estradiol. The dosage and sacrifice schedule, and the method of determining uterine weights and reporting data, were the same as the methods described above under Test 1.

TABLE II

| Treatment | Uterine weight |
|---|---|
| *Mature ovariectomized mice* | |
| Experiment A | |
| Control | 12.3 mg. |
| Estradiol, 0.3 mcg., s.c. | 65.9 |
| Example 3, 0.3 mcg., s.c. | 54.9 |
| Example 3, 3 mcg., s.c. | 48.7 |

TABLE II-continued

| Treatment | Uterine weight |
|---|---|
| Example 3, 30 mcg., s.c. | 31.1 |
| Example 3, 300 mcg., s.c. | 22.1 |
| Example 3, 3 mg., s.c. | 21.3 |
| *Immature mice* | |
| Experiment B | |
| Control | 10.6 mg. |
| Estradiol, 0.3 mcg., s.c. | 50.3 |
| Example 3, 0.03 mcg., s.c. | 41.3 |
| Example 3, 0.3 mcg., s.c. | 40.6 |
| Example 3, 3 mcg., s.c. | 26.5 |
| Example 3, 30 mcg., s.c. | 18.9 |
| Example 3, 300 mcg., s.c. | 14.6 |
| Example 3, 3 mg., s.c. | 13.9 |
| *Immature rats* | |
| Experiment C | |
| Control | 23.8 mg. |
| Estradiol, 0.3 mcg., s.c. | 56.8 |
| Example 3, 3 mcg., oral | 55.0 |
| Example 3, 30 mcg., oral | 46.7 |
| Example 3, 300 mcg., oral | 31.3 |
| Example 3, 3 mg., oral | 30.6 |
| Experiment D | |
| Control | 21.1 mg. |
| Estradiol, 0.3 mcg., s.c. | 71.5 |
| Example 3, 3 mcg., s.c. | 53.6 |
| Example 3, 30 mcg., s.c. | 33.7 |
| Example 3, 300 mcg., s.c. | 30.7 |
| Example 3, 3 mg., s.c. | 28.0 |
| Experiment E | |
| Control | 30.0 mg. |
| Estradiol, 0.09 mcg., s.c. | 44.9 |
| Example 3, 3 mcg., s.c. | 42.5 |
| Example 3, 30 mcg., s.c. | 35.8 |
| Example 3, 300 mcg., s.c. | 33.7 |
| Example 3, 3 mg., s.c. | 31.0 |
| Experiment F | |
| Control | 30.0 mg. |
| Estradiol, 0.15 mcg., s.c. | 50.9 |
| Example 3, 3 mcg., s.c. | 49.4 |
| Example 3, 30 mcg., s.c. | 40.9 |
| Example 3, 300 mcg., s.c. | 36.5 |
| Example 3, 3 mg., s.c. | 36.2 |
| Experiment G | |
| Control | 24.8 |
| Estradiol, 3 mcg., s.c. | 84.4 |
| Example 3, 3 mcg., s.c. | 71.9 |
| Example 3, 30 mcg., s.c. | 42.2 |
| Example 3, 300 mcg., s.c. | 33.7 |
| Example 3, 3 mg., s.c. | 30.2 |
| Experiment H | |
| Control | 24.8 mg. |
| Estradiol, 30 mcg., s.c. | 113.2 |
| Example 3, 3 mcg., s.c. | 92.7 |
| Example 3, 30 mcg., s.c. | 60.2 |
| Example 3, 300 mcg., s.c. | 48.9 |
| Example 3, 3 mg., s.c. | 33.1 |
| Experiment I | |
| Control | 25.4 mg. |
| Estradiol, 0.3 mcg., s.c. | 63.1 |
| Example 9, 3 mg., s.c. | 38.1 |
| Example 10, 3 mg., s.c. | 32.2 |
| Example 11, 3 mg., s.c. | 40.0 |
| Example 12, 3 mg., s.c. | 31.8 |
| Example 13, 3 mg., s.c. | 41.1 |
| Example 14, 3 mg., s.c. | 37.5 |

The following test was carried out to determine if the compounds of this invention could reverse an estrogenic response, when administration of the compound was started after the estrogenic response had become established.

Test 3

Regression Tests

The same basic scheme of Tests 1 and 2 was followed in this experiment, except that the administration of estradiol was begun before the administration of the compound of Example 3 above. The test animals were immature rats, and all administrations were by subcutaneous injection.

The mean uterine weight of the untreated control animals was 20.9 mg.

Estradiol alone was administered to groups of animals at the rate of 0.1 mcg./day for three, four, six, and eight days, and each group of animals was sacrificed on the day after the last treatment day. The mean uterine weights of these groups of animals, respectively, were 97.9, 97.3, 119.9 and 112.3 mg.

One group of compound-treated animals was given estradiol at 0.1 mcg./day for three days, and was given 0.1 mcg. of estradiol and 1 mg. of the compound of this invention on the fourth day. The animals were sacrificed on the fifth day and their mean uterine weight was 56.4 mg.

Another group of treated animals was given 0.1 mcg. of estradiol per day for three days and was given 0.1 mcg. of estradiol and 1 mg. of the compound of this invention on each of the following three days. The animals were sacrificed on the seventh day and their mean uterine weight was 57.0 mg.

A final group of compound-treated animals was given 0.1 mcg. of estradiol on each of three days, and was then given 0.1 mcg. of estradiol and 1 mg. of the compound of this invention on each of the following five days. They were sacrificed on the ninth day and their mean uterine weight was found to be 50.7 mg.

Another group of control animals was sacrificed on the ninth day of this experiment, since the animals had been growing through the long period of the experiment, and their mean uterine weight was found to be 31.1 mg.

The results of the experiments reported in this test clearly show that the compounds of this invention are capable of reversing an established estrogenic response when the compounds are administered after the response is established.

Additional experiments have been done to determine the ability of the compounds of this invention to bind to the estrogen-receptor, and their rate of dissociation from the receptor, relative to the rate of dissociation of estradiol.

Test 4

Relative Binding Affinity Tests

A group of immature 40–45 g. female laboratory rats of a standardized strain were sacrificed, and their uteri were promptly removed and dissected free of adhering fat and other extraneous tissue. The uteri, which were constantly kept cold, were homogenized in a buffer which contained 10 mM tris(hydroxymethyl)aminomethane, hydrochloride and 1.5 mM ethylenediaminetetraacetic acid at pH 7.4, at a concentration of 1 uterus/ml. The homogenate was then centrifuged for one hour at 100,000×G at 4° C., and the supernatant, containing the cytosol fraction, was retained.

One-half ml. of the cytosol preparation was added to each of a group of tubes which contained 10 nM of 2,4,6,7-$^3$H estradiol, or the labeled estradiol plus log concentrations from 10 to 1000 nM of unlabeled competitor which could be the compound to be tested, that of Example 3, or additional, unlabeled, estradiol. All assays were performed in duplicate, and all assays in a given experimental group were carried out on aliquots from the same pool of cytosol preparation.

Samples were then mixed and incubated at specified temperatures. Each incubation was ended at the specified time by cooling the sample and adding 0.5 ml. of a dextran-coated charcoal suspension containing 10 mM tris(hydroxymethyl)aminomethane, hydrochloride, 1 mM of ethylenediaminetetraacetic acid, 1% of charcoal and 0.1% of dextran at pH 8. The samples were agitated frequently for fifteen minutes at 4° C., and then centrifuged at 800×G at the same temperature for fifteen minutes. The supernatant from the centrifugation contained the cytosol preparation, free of unbound estradiol and estradiol-competitors, which were adsorbed by the charcoal.

Each one-half ml. aliquot of supernatant was transferred to a 20 ml. vial of scintillation solution, and DPM was measured by liquid scintillation spectrometry. The difference between total DPM in control samples containing only labeled estradiol, and that observed in the presence of 1000 nM of unlabeled estradiol was considered to be specific binding. The concentration of unlabeled estradiol on the inhibition curve which corresponded to 50% inhibition of specific binding was determined, as was the concentration on the inhibition curve of the compound of this invention which corresponded to 50% inhibition of specific binding. Relative binding affinity (RBA) was calculated as the concentration of estradiol which gave 50% inhibition, divided by the concentration of the test compound which gave 50% inhibition.

Experiments were carried out at 4°, 15° and 30° C., and for periods of one half hour, one hour and 24 hours in various tests. The table below lists the relative binding affinities which were found in a number of experiments, carried out as described above, at the various conditions listed in the headings of the table.

TABLE III

| Experiment | 4° C., 1 hour | 4° C., 24 hours | 15° C., 1 hour | 30° C., ½ hour |
|---|---|---|---|---|
| 1 | 1.6 | 1.03 | 0.6 | 1.2 |
| 2 | 1.7 | 1.9 | 1.9 | 2.3 |
| 3 | 3.7 | 1.2 | 1.7 | 2.5 |
| 4 | 1.1 | 1.5 | 1.9 | 3.8 |
| 5 | 2.7 | 2.0 | 1.9 | 2.0 |
| 6 | 0.8 | 1.3 | 0.9 | 1.9 |
| 7 | 0.6 | 4.0 | 2.3 | — |
| 8 | <0* | 1.2 | 0.8 | 1.8 |
| 9 | 0.9 | 0.9 | — | 1.2 |
| 10 | 1.3 | 4.2 | — | 3.2 |

*In this test, no concentration of the test compound achieved 50% inhibition.

The compounds of this invention have also been tested to determine the facility with which they dissociate from the estrogen receptor.

Test 5

Dissociation Tests

A cytosol preparation was made as described in Test 4, but at a concentration of 2 uteri per ml. One-half ml. aliquots of the cytosol preparation were incubated for one hour at 4° C. with 2,000 nM of the compound of Example 3, or of unlabeled estradiol. After one hour, 0.5 ml. of dextran-coated charcoal suspension was added, the samples were agitated frequently for fifteen minutes, and were then centrifuged at 800×G at 4° C. for fifteen minutes to remove unbound molecules. One-half ml. aliquots of the treated cytosol preparation were then transferred to two sets of tubes, one containing 10 nM of labeled estradiol and the other containing 1,000 nM of unlabeled estradiol as well as 10 nM of labeled estradiol. Two sets of samples were run for each condition.

The samples were then incubated at specified temperatures and times, and were terminated at the end of the designated times by cooling them in an ice bath and adding 0.5 ml. of the dextran-coated charcoal suspension to each. The samples were agitated and centrifuged, and 0.5 ml. of supernatant from each was added to scintillation fluid for determination of DPM as described under Test 4. The DPM observed in samples containing 1,000 nM of unlabeled estradiol was subtracted from the readings for corresponding samples with labeled estradiol only, to determine specific binding for each condition. The percent difference in specifically bound DPM between the cytosol exposed to the compound of this invention, or of unlabeled estradiol, and unexposed controls, at each time point was determined and expressed as relative percent bound for the compound and for estradiol.

TABLE IV

| Experiment | | 1 min. | 5 min. | 15 min. | 30 min. | 1 hour | 2 hours |
|---|---|---|---|---|---|---|---|
| | | | | 30° C. | | | |
| A | Compound | 61% | 70% | 50% | 26% | 3% | 19% |
| | Estradiol | 63% | 45% | 46% | 47% | 24% | 43% |
| B | Compound | 76% | 71% | 55% | 48% | 38% | 40% |
| | Estradiol | 87% | 64% | 37% | 33% | 15% | 14% |
| C | Compound | 50% | 54% | 34% | 24% | 20% | 24% |
| | Estradiol | 62% | 48% | 24% | 18% | 6% | 1% |
| D | Compound | 52% | 58% | 43% | 38% | 33% | 20% |
| | Estradiol | 64% | 54% | 18% | 25% | 21% | 24% |
| E | Compound | 67% | 57% | 43% | 20% | 16% | 26% |
| | Estradiol | 67% | 38% | 41% | 23% | 10% | 22% |
| F | Compound | 53% | 67% | 68% | 57% | 55% | 53% |
| | Estradiol | 51% | 45% | 35% | 34% | 24% | 5% |
| | | | | 4° C. | | | |
| G | Compound | 76% | 72% | 58% | 76% | 64% | 65% |
| | Estradiol | 81% | 77% | 67% | 66% | 57% | 52% |
| H | Compound | 65% | 65% | 42% | 71% | 77% | 0 |
| | Estradiol | 73% | 76% | 63% | 57% | 61% | 63% |
| I | Compound | 67% | 68% | 93% | 80% | 77% | 62% |
| | Estradiol | 51% | 80% | 85% | 76% | 93% | 77% |
| J | Compound | 43% | 9% | 93% | 77% | 100% | 74% |
| | Estradiol | 26% | 71% | 85% | 70% | 74% | 68% |
| K | Compound | 37% | 36% | 60% | 55% | 60% | 64% |
| | Estradiol | 68% | 48% | 52% | 51% | 35% | 46% |
| L | Compound | 58% | 54% | 53% | 72% | 57% | 58% |
| | Estradiol | 58% | 66% | 48% | 65% | 60% | 58% |

The above data clearly show that the representative compound of this invention which was tested has a high affinity for the estrogen receptor, and dissociates from it less readily than does estradiol.

The effect of a representative compound of this invention against mammary tumors in the rat has been determined in tests carried out as follows.

Test 6

Tests Against DMBA-Induced Tumors

Mammary tumors were induced in adult female virgin rats by a single 20-mg. oral dose of 7,12-dimethylbenzanthracene. Within about six weeks, visible and palpable tumors were present in the mammary tissue of the rats, and the rats were allocated into treatment and control groups in such a way that each group contained animals having approximately the same size and number of tumors. The size of the tumors was estimated by measuring their cross-sectional area.

At the end of the test, the animals were ovariectomized, all treatments were stopped, and the animals were observed to determine if the tumors regressed, due to the lack of estrogen in the system. Most of the DMBA-induced tumors evidently were estrogen-dependent, because most of them immediately regressed upon ovariectomy. Exceptions, where the tumors did not regress after ovariectomy, are foot-noted in the reports of individual experiments below.

Experiment A

In this experiment, 6-hydroxy-2-(4-hydroxyphenyl)-3-[4-(2-piperidinoethoxy)benzoyl]benzo[b]thiophene was administered orally to each animal for eight weeks. In the first two-week period, the animals were given 0.1 mg./kg./day, which dose was increased to 5, 10 and 20 mg./kg./day in successive two-week intervals. The control animals were handled each day and given an oral dose of 0.5 ml. of corn oil, as a blank. At the end of the eight-week period, the tumors of the control animals had total cross-sectional areas which averaged 1957 square millimeters, and ranged from 512 square millimeters to 4030 square millimeters.

The animals which had been treated with the compound of this invention, in contrast, had an average total cross-sectional area of tumor of 345 square millimeters, ranging from complete regression to one animal having 1550 sq. mm. total cross-sectional area. The tumors of this animal, however, were not estrogen-dependent, and did not regress when the animal was ovariectomized. One animal in the compound-treated group could not be evaluated, because its tumors had changed to an impalpable form, or, perhaps, had completely regressed but had left some abnormalities in the tissue after its regression.

Experiment B

In this experiment, the same compound was administered at 20 mg./kg./day, orally, for four weeks. In other respects, the test was run in the same way as that of Experiment A above. At the end of the four weeks, the average total tumor area of the control animals was 487 square millimeters, ranging from 178 to 886 square millimeters. The tumors of one of the compound-treated animals had completely regressed, with no palpable tumor present at the end of the four-week period; the other five animals had tumor areas from 16 to 668 square millimeters; the average total area of the treated animals was 152 square millimeters. The large tumor of the compound-treated animal having an area of 668 square millimeters was found to shrink after ovariectomy, but its growth had been checked, and it had not significantly grown, since the second week of the experiment. Thus, it was apparently a partially estrogen-dependent tumor.

Experiment C

This experiment was also carried out for four weeks, and two groups of treated animals were used. One group of animals received 20 mg./kg./day of the same compound used in Experiments A and B, and the other received 40 mg./kg./day. The animals were not ovariectomized at the end of the experiment.

At the end of the four weeks, the control animals, of which there were ten, were found to have an average total tumor area of 958 square millimeters, ranging from 168 to 2,094 square millimeters. The average cross-sectional tumor area of the animals which received the low dose of the compound of this invention was 441 square millimeters, with a range from no tumors present to 1907 square millimeters. The animals which received the high dose of the compound had even smaller tumors, averaging 304 square millimeters, with a range from 116 to 758 square millimeters.

Experiment D

This experiment was followed for five weeks. The treated animals received 1 mg./kg. per day of 6-methoxy-2-(4-hydroxyphenyl)-3-[4-(2-piperidinoethoxy)benzoyl]benzo[b]thiophene, hydrochloride, as a subcutaneous injection in corn oil. The animals were not ovariectomized at the end of the experiment.

At the end of four weeks, the seven control animals had an average total tumor area of 1,446 square millimeters, ranging from 592 to 2,400. At the end of five weeks, the tumors of two of the control animals had burst and were unmeasurable; the tumors of the other five controls averaged 1,487 square millimeters in total area, ranging from 966 to 2,123.

The tumors of three of the eight treated animals had completely regressed by the fourth week of the test; the average total tumor area of the treated group was 692 square millimeters. If one animal having a tumor area of 3764 sq. mm. is ignored, the average tumor area of the other seven is 254 sq. mm.

At the fifth week of the test, the largest tumors of the treated animal having the largest total at four weeks had burst and were unmeasurable. The other seven treated animals averaged 398 square millimeters, ranging from the three completely regressed animals to one with a single 1974 sq. mm. tumor.

Test 7

Anti-Androgen Tests

The antiandrogenic property of the compounds was evaluated in the following tests, in which the compound of Example 3 was used again.

Experiment A

The animals used in this test were adult male rats having a body weight which averaged about 330 g. when the experiment ended. All of the animals to be used in the experiment were castrated by the scrotal route, and were held untreated for 3 days. On the fourth day, subcutaneous administration of 0.1 mg./day of an exogenous androgen, testosterone propionate, was begun, and was continued for seven consecutive days. An untreated control group of animals received injections of 0.1 ml./day of corn oil as a blank treatment. The compound of this invention was administered orally or subcutaneously to the treated animals in 0.1 ml. of corn oil, at the same time that the androgen was administered. The animals were sacrificed 24 hours after the last injection of testosterone propionate, the ventral prostate glands were removed and weighed, and the mean of the weights of each treatment group was reported. The table below reports the mean weights resulting from administration of various doses of the compound along with androgen.

Each treatment group of animals in this experiment consisted of seven to nine animals, except for the untreated control group, which contained twelve animals.

The results of the experiment were as follows.

| Treatment | Mean Prostate Weight |
|---|---|
| Untreated control | 40 mg. |
| Androgen only | 309 |
| 1 mg./day compound, S.C. | 201 |
| 0.1 mg./day compound, S.C. | 235 |
| 0.01 mg./day compound, S.C. | 253 |
| 1 mg./day compound, oral | 242 |
| 0.1 mg./day compound, oral | 267 |
| 0.01 mg./day compound, oral | 192 |

Experiment B

This experiment was carried out in the same manner as Experiment A above, except that the test animals were immature male rats, weighing about 120 g. each at sacrifice. Each treatment group consisted of six or seven animals. All treatments in this experiment were administered by subcutaneous injection. The amount of the androgen administered was only 20 mcg./day because of the small size of the animals.

| Treatment | Mean Prostate Weight |
|---|---|
| Untreated control | 12.6 mg. |
| Androgen only | 48.7 |
| 5 mg./kg./day compound | 36.6 |
| 0.5 mg./kg./day compound | 33.8* |

*One animal in this group had a surprisingly large prostate weighing 54 mg. If this animal is excluded from the group, the average weight is 30.5.

Experiment C

This experiment was also conducted in immature rats having average body weight of about 115 g. when the experiment ended. In other respects, the experiment was as described under Experiment B above. The treatment groups consisted of ten animals each, except for the androgen only group, of 16 animals, and the 5 mg./kg. group, of nine animals.

| Treatment | Mean Prostate Weight |
|---|---|
| Untreated control | 11.4 mg. |
| Androgen only | 43.5 |
| 5 mg./kg./day compound | 29.0 |
| 0.5 mg./kg./day compound | 31.1 |
| 0.05 mg./kg./day compound | 34.0 |

The experiments above show clearly that the representative compound of this invention in the tests inhibited a large part of the abnormal prostate growth caused by the administration of exogenous androgen, and therefore that the compounds of this invention are of interest and importance in the treatment of androgen-dependent abnormal conditions, especially benign prostatic hypertrophy and prostatic cancer.

As has been stated, this invention provides a method of alleviating a pathological condition of an endocrine target organ, which condition is dependent or partially dependent on an estrogen or on an androgen, which comprises administering an effective dose of a compound as described above to a subject suffering from such a condition or at risk of suffering from such a condition.

The preferred compounds of this invention are 6-hydroxy-2-(4-hydroxyphenyl)-3-[4-(2-piperidinoethoxy)benzoyl]benzo[b]thiophene and its physiologically acceptable salts, especially the hydrochloride. Other preferred compounds include 6-acetoxy-2-(4-acetoxyphenyl)-3-[4-(2-piperidinoethoxy)benzoyl]benzo[b]-thiophene, 6-ethoxycarbonyloxy-2-(4-ethoxycarbonyloxyphenyl)-3-[4-(2-piperidnoethoxy)benzoyl]benzo[b]thiophene, 6-benzoyloxy-2-(4-benzoyloxyphenyl)-3-[4-(2-piperidinoethoxy)benzoyl]benzo[b]thiophene and 6-methoxy-2-(4-methoxyphenyl)-3-[4-(2-piperidinoethoxy)benzoyl]benzo[b]thiophene, and their physiologically acceptable salts, especially the hydrochlorides.

The effect of the compounds of this invention is described as alleviating the pathological conditions, to indicate that complete cure of the conditions cannot always be expected, but that use of an effective dose of the compounds will benefit the subject by causing at least some regression of the condition. When the compounds are used preventively, as in a subject who has suffered from an occurrence of mammary fibrocystic disease and is at risk of further occurrences, the compounds will prevent such occurrences or, at least, lessen or delay the severity of their effects.

Use in human subjects is preferred.

The compounds of this invention are improved antiestrogens, compared to earlier compounds, because they have a higher ability to inhibit estrogenic response and have less inherent estrogenicity than the earlier compounds. The compounds of this invention, accordingly, give a greater antiestrogenic effect for a given dose of compound, inhibit more effectively at the optimum dose, and contribute less incidental estrogenic response than any prior-known antiestrogen. Their antiandrogenic properties, combined with their antiestrogenic properties, make the compounds of this invention still more unique.

It is believed that the present compounds are relatively quite free of a histological side-effect common to earlier anti-estrogens. Tamoxifen, for example, causes abnormal growth of uterine epithelial cells. Preliminary studies indicate that the present compounds either cause no abnormality of epithelial cells of the uterus, or cause only extremely slight abnormal growth.

The exact mechanism of an antiestrogen in treating mammary cancer is not known. It is believed, however, that the antiestrogen, circulating in the body, competes with endogenous estrogens for estrogen receptor sites in the cancer. To be effective, the antiestrogen must find and bind to receptor sites, and prevent estradiol from occupying them. Clearly, if the antiestrogen has inherent estrogenicity of its own, it is likely to enable the cancer to grow just as if the cancer had absorbed endogenous estrogen.

The biological tests reported above show the low estrogenicity, high antiestrogenicity and strong affinity for estrogen receptor sites of the compounds of this invention.

Accordingly, a most important embodiment of the present invention is a method of alleviating mammary cancers which comprises administering a compound of this invention at an effective rate to a patient suffering from or at risk of such a cancer.

The antiestrogens of this invention are believed to have other biological effects as well. Antiestrogens play a role in the treatment of fibrocystic disease of the mammary glands, which role is as yet less well defined than is their use in the treatment of mammary cancers. It is believed, however, that fibrocystic disease, which manifests itself in benign lumps or growths in mammary tissue, is estrogen-dependent. It has been established that the administration of antiestrogens to patients who have or who have shown a tendency toward fibrocystic disease can alleviate it by both causing the regression of the symptoms of it, and preventing its recurrence. Accordingly, the administration of a compound of this invention to a patient having or at risk of fibrocystic disease to alleviate the disease, is an important embodiment of the invention.

Further, the tests presented above illustrate that the compounds of this invention have an important antiandrogenic effect on the prostate gland. Benign prostatic hypertrophy is a very common and distressing condition, manifested by abnormal growth of the prostate gland. An effective drug for the control of this condition has long been sought. The tests reported above show that compounds of this invention have a strong effect on androgen stimulation and maintenance of the size of the prostate gland. Accordingly, it is expected that the compounds of this invention can be administered to males suffering from or at risk of benign prostatic hypertrophy to alleviate the condition. The method of alleviating benign prostatic hypertrophy by administering an effective dose of a compound of this invention is, accordingly, an important embodiment of the invention.

Similarly, use of anti-androgens in patients suffering from prostatic cancer is known to interrupt the progression of the cancer, because prostatic cancer is dependent upon androgen for its growth, and the anti-androgenic compounds of this invention interrupt the course of the disease by preventing the cancer from utilizing endogenous androgen in the patient's system. The exact mode of action of the compounds as anti-androgens has not been elucidated, but the in vivo tests reported above show clearly that the compounds are, indeed, antiandrogens. Accordingly, the use of the compounds of this invention to alleviate prostatic cancer is another important embodiment of the invention.

The tests which have been applied to a representative compound of this invention were carried out in standard laboratory animals, as described above. The tests which have been applied to the compounds are believed to be clearly predictive of beneficial effects in humans, based on the effects in laboratory animals.

The dose of a compound of this invention to be administered to a human is rather widely variable. It should be noted that it may be necessary to adjust the dose of a compound when it is administered in the form of a salt, such as a laurate, the salt-forming moiety of which has an appreciable molecular weight. The general range of effective administration rates of the compounds is from about 0.05 mg./kg./day to about 50 mg./kg./day. A preferred rate range is from about 0.1 mg./kg./day to about 10 mg./kg./day, and the most highly preferred range is from about 0.1 mg./kg./day to about 5 mg./kg./day. Of course, it is often practical to administer the daily dose of a compound in portions, at various hours of the day.

The route of administration of the compounds of this invention is not critical. The compounds are known to be absorbed from th alimentary tract, and so it is usually preferred to administer a compound orally for reasons of convenience. However, the compounds may equally effectively be administered percutaneously, or as suppositories for absorption by the rectum, if desired in a given instance.

The compounds of this invention are usually administered as pharmaceutical compositions which are important and novel embodiments of the invention because of the presence of the compounds. All of the usual types of compositions may be used, including tablets, chewable tablets, capsules, solutions, parenteral solutions, troches, suppositories and suspensions. Compositions are formulated to contain a daily dose, or a convenient fraction of a daily dose, in a dosage unit, which may be a single tablet or capsule or a convenient volume of a liquid. In general, compositions contain from about 0.000006% of compound, depending on the desired dose and the type of composition to be used.

The activity of the compounds does not depend on the compositions in which they are administered or on the concentration of the composition. Thus, the compositions are chosen and formulated solely for convenience and economy.

Any of the compounds may be readily formulated as tablets, capsules and the like; it is preferable to prepare solutions from water-soluble salts, such as the hydrochloride salt.

In general, all of the compositions are prepared according to methods usual in pharmaceutical chemistry. Some discussion will be provided, followed by a group of typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly-soluble pellet of the compound may be prepared and incorporated in a tablet or capsule. The techique may be improved by making pellets of several different dissolution rates and filling capsules with a mixture of the pellets. Tablets or capsules may be coated with a film which resists dissolution for a predictable period of time. Even parenteral preparations may be made long-acting, by dissolving or suspending the compound in oily or emulsified vehicles which allow it to disperse only slowly into the serum.

The following typical formulae are provided further to assist the formulations chemist.

| Capsules | |
|---|---|
| 6-hydroxy-2-(4-hydroxyphenyl)-3-[4-(2-piperidinoethoxy)benzoyl]benzo[b]-thiophene, hydrochloride | 3 mg. |
| Microcrystalline cellulose | 400 |
| Pregelatinized starch | 95 |
| Silicone fluid | 2 |
| 6-methoxy-2-(4-methoxyphenyl)-3-[4-(2-piperidinoethoxy)benzoyl]benzo[b]-thiophene, acetate | 150 mg. |
| Pregelatinized starch | 106 |
| Starch | 52 |
| Silicone fluid | 1.6 |
| 6-acetoxy-2-(4-acetoxyphenyl)-3-[4-(2-piperidinoethoxy)benzoyl]benzo[b]-thiophene, hydrochloride | 300 mg. |
| Pregelatinized starch | 200 |
| Solutions | |
| 6-hydroxy-2-(4-hydroxyphenyl)-3-[4-(2-piperidinoethoxy)benzoyl]benzo[b]-thiophene, hydrochloride | 3 mg. |
| Purified water | 5 cc. |
| 6-hydroxy-2-(4-hydroxyphenyl)-3-[4-(2-piperidinoethoxy)benzoyl]benzo[b]-thiophene, hydrochloride | 20 mg. |
| Purified water | 5 cc. |
| Tablets | |
| 6-cyclopentoxy-2-(4-cyclopentoxyphenyl)-3-[4-(2-piperidinoethoxy)benzoyl]benzo[b]-thiophene | 5 mg. |
| Microcrystalline cellulose | 240 |
| Starch | 45 |
| Stearic acid | 6 |
| Magnesium stearate | 3 |
| Colloidal silicon dioxide | 1 |
| 6-benzyloxy-2-(4-benzyloxyphenyl)-3-[4-(2-piperidinoethoxy)benzoyl]benzo[b]-thiophene, benzoate | 150 mg. |
| Microcrystalline cellulose | 128 |
| Lactose | 25 |
| Pregelatinized starch | 10 |
| Stearic acid | 8 |
| Magnesium stearate | 3 |
| Colloidal silicon dioxide | 2 |
| 6-ethoxycarbonyloxy-2-(4-ethoxycarbonyloxyphenyl)-3-[4-(2-piperidinoethoxy)benzoyl]benzo[b]thiophene | 250 mg. |
| Calcium phosphate | 58 |
| Lactose | 54 |
| Microcrystalline cellulose | 31 |

-continued

| Starch | 5 |
| Stearic acid | 2 |
| Magnesium stearate | 1 |

I claim:
1. A compound of the formula

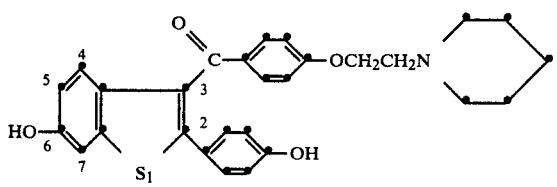

a physiologically acceptable ester or ether thereof, or a physiologically acceptable acid addition salt thereof.

2. A compound of claim 1 of the formula

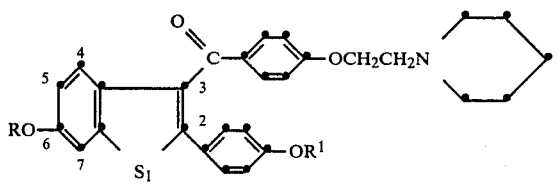

wherein R and $R^1$ independently are hydrogen, —$COR^2$ or $R^3$;

$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl;

$R^3$ is $C_1$–$C_4$ alkyl, $C_5$–$C_7$ cycloalkyl or benzyl; or a physiologically acceptable acid addition salt thereof.

3. The compound of claim 2 which is 6-hydroxy-2-(4-hydroxyphenyl)-3-[4-(2-piperidinoethoxy)benzoyl]benzo[b]thiophene, or a physiologically acceptable acid addition salt thereof.

4. A compound of claim 2 wherein R and $R^1$ are the same, and are a group other than hydrogen.

5. A compound of claim 2 wherein one of R and $R^1$ is hydrogen.

6. A compound of claim 2 wherein one or both of R and $R^1$ is —$COR^2$.

7. A compound of claim 2 wherein one or both of R and $R^1$ is $R^3$.

8. A compound of any one of claims 2, 4 or 6 wherein $R^2$ is $C_1$–$C_{14}$ alkyl.

9. A compound of any one of claims 2, 4 or 6 wherein $R^2$ is $C_1$–$C_3$ chloroalkyl or $C_1$–$C_3$ fluoroalkyl.

10. A compound of any one of claims 2, 4 or 6 wherein $R^2$ is $C_5$–$C_7$ cycloalkyl.

11. A compound of any one of claims 2, 4 or 6 wherein $R^2$ is $C_1$–$C_4$ alkoxy.

12. A compound of any one of claims 2, 4 or 6 wherein $R^2$ is phenyl.

13. A compound of any one of claims 2, 4 or 6 wherein $R^2$ is substituted phenyl.

14. A compound of any one of claims 2, 4, 5 or 7 wherein $R^3$ is $C_1$–$C_4$ alkyl.

15. A compound of any one of claims 2, 4, 5 or 7 wherein $R^3$ is $C_5$–$C_7$ cycloalkyl.

16. A compound of any one of claims 2, 4, 5 or 7 wherein $R^3$ is benzyl.

17. A compound of any one of claims 1–7 which is a free base.

18. A compound of any one of claims 1–7 which is a physiologically acceptable acid addition salt.

19. A compound of any one of claims 1–7 which is a hydrochloride.

20. The compound of claim 1 which is 6-acetoxy-2-(4-acetoxyphenyl)-3-[4-(2-piperidinoethoxy)benzoyl]benzo[b]thiophene, or a physiologically acceptable acid addition salt thereof.

21. The compound of claim 1 which is 6-benzoyloxy-2-(4-benzoyloxyphenyl)-3-[4-(2-piperidinoethoxy)benzoyl]benzo[b]thiophene, or a physiologically acceptable acid addition salt thereof.

22. The compound of claim 1 which is 6-ethoxycarbonyloxy-2-(4-ethoxycarbonyloxyphenyl)-3-[4-(2-piperidinoethoxy)benzoyl]benzo[b]thiophene, or a physiologically acceptable acid addition salt thereof.

23. The compound of claim 1 which is 6-methoxy-2-(4-methoxyphenyl)-3-[4-(2-piperidinoethoxy)benzoyl]benzo[b]thiophene, or a physiologically acceptable acid addition salt thereof.

24. An antiestrogenic and antiandrogenic pharmaceutical composition comprising a pharmaceutically acceptable diluent and an effective amount of a compound of the formula

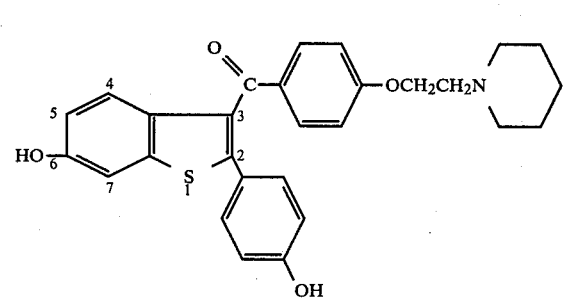

a physiologically acceptable ester or ether thereof, or a physiologically acceptable acid addition salt thereof.

25. A composition of claim 24 wherein the compound is of the formula

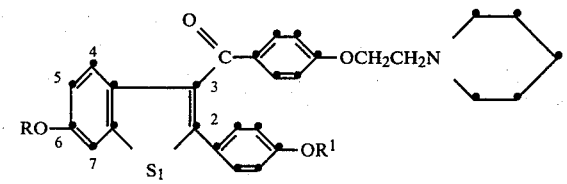

wherein R and $R^1$ independently are hydrogen, —$COR^2$ or $R^3$;

$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl;

$R^3$ is $C_1$–$C_4$ alkyl, $C_5$–$C_7$ cycloalkyl or benzyl; or a physiologically acceptable acid addition salt thereof.

26. A composition of claim 25 wherein the compound is 6-hydroxy-2-(4-hydroxyphenyl)-3-[4-(2-piperidinoethoxy)benzoyl]benzo[b]thiophene, or a physiologically acceptable acid addition salt thereof.

27. A composition of claim 26 wherein the compound is the hydrochloride.

28. A composition of claim 25 wherein the compound is a compound wherein R and $R^1$ are the same, and are a group other than hydrogen.

29. A composition of claim 28 wherein the compound is a compound wherein R and $R^1$ are —$COR^2$.

30. A composition of claim 29 wherein the compound is a compound wherein $R^2$ is $C_1$–$C_{14}$ alkyl.

31. A composition of claim 30 wherein the compound is 6-acetoxy-2-(4-acetoxyphenyl)-3-[4-(2-piperidinoethoxy)benzoyl]benzo[b]thiophene, or a physiologically acceptable acid addition salt thereof.

32. A composition of claim 29 wherein the compound is a compound wherein $R^2$ is phenyl.

33. A composition of claim 32 wherein the compound is 6-benzoyloxy-2-(4-benzoyloxyphenyl)-3-[4-(2-piperidinoethoxy)benzoyl]benzo[b]thiophene, or a physiologically acceptable acid addition salt thereof.

34. A composition of claim 29 wherein the compound is a compound wherein $R^2$ is $C_1$–$C_4$ alkoxy.

35. A composition of claim 34 wherein the compound is 6-ethoxycarbonyloxy-2-(4-ethoxycarbonyloxyphenyl)-3-[4-(2-piperidinoethoxy)benzoyl]benzo[b]thiophene, or a physiologically acceptable acid addition salt thereof.

36. A composition of claim 28 wherein R and $R^1$ and $R^3$.

37. A composition of claim 36 wherein the compound is 6-methoxy-2-(4-methoxyphenyl)-3-[4-(2-piperidinoethoxy)benzoyl]benzo[b]thiophene, or a physiologically acceptable acid addition salt thereof.

38. A composition of claim 25 wherein the compound is a compound wherein one of R and $R^1$ is hydrogen.

39. A method of alleviating a pathological condition of an endocrine target organ, which condition is dependent or partially dependent on an estrogen or on an androgen, which comprises administering to a subject suffering from such a condition an effective dose of a compound of the formula a physiologically acceptble ester or ether thereof, or a physiologically acceptable acid addition salt thereof.

40. A method of claim 39 wherein the pathological condition is dependent or partially dependent on an estrogen.

41. A method of claim 40 wherein the dose of the compound is from about 0.05 mg./kg./day to about 50 mg./kg./day.

42. A method of claim 41 wherein the target organ is the breast, and the pathological condition is mammary cancer.

43. A method of claim 42 wherein the dose of the compound is from about 0.1 mg./kg./day to about 10 mg./kg./day.

44. A method of claim 41 wherein the target organ is the breast, and the pathological condition is fibrocystic disease.

45. A method of claim 44 wherein the dose of the compound is from about 0.1 mg./kg./day to about 10 mg./kg./day.

46. A method of claim 39 wherein the pathological condition is dependent or partially dependent on an androgen.

47. A method of claim 46 wherein the dose of the compound is from about 0.05 mg./kg./day to about 50 mg./kg./day.

48. A method of claim 47 wherein the target organ is the prostate, and the pathological condition is prostatic cancer.

49. A method of claim 48 wherein the dose of the compound is from about 0.1 mg./kg./day to about 10 mg./kg./day.

50. A method of claim 47 wherein the target organ is the prostate, and the pathological condition is benign prostatic hypertrophy.

51. A method of claim 50 wherein the dose is from about 0.1 mg./kg./day to about 10 mg./kg./day.

52. A method of any one of claims 39–51 wherein the compound is of the formula wherein R and $R^1$ independently are hydrogen, —$COR^2$ or $R^3$;

$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl;

$R^3$ is $C_1$–$C_4$ alkyl, $C_5$–$C_7$ cycloalkyl or benzyl; or a physiologically acceptable acid addition salt thereof.

53. A method of claim 52 wherein the compound is 6-hydroxy-2-(4-hydroxyphenyl)-3-[4-(2-piperidinoethoxy)benzoyl]benzo[b]thiophene, or a physiologically acceptable acid addition salt thereof.

54. A method of claim 53 wherein the compound is the hydrochloride.

55. A method of claim 52 wherein the compound is a compound wherein R and $R^1$ are the same, and are a group other than hydrogen.

56. A method of claim 55 wherein the compound is a compound wherein R and $R^1$ are —$COR^2$.

57. A method or claim 56 wherein the compound is 6-acetoxy-2-(4-acetoxyphenyl)-3-[4-(2-piperidinoethoxy)benzoyl]benzo[b]thiophene, or a physiologically acceptable acid addition salt thereof.

58. A method of claim 56 wherein the compound is 6-benzoyloxy-2-(4-benzoyloxyphenyl)-3-[4-(2-piperidinoethoxy)benzoyl]benzo[b]thiophene, or a physiologically acceptable acid addition salt thereof.

59. A method of claim 56 wherein the compound is 6-ethoxycarbonyloxy-2-(4-ethoxycarbonyloxyphenyl)-3-[4-(2-piperidinoethoxy)benzoyl]benzo[b]thiophene, or a physiologically acceptable acid addition salt thereof.

60. A method of claim 55 wherein the compound is a compound wherein R and $R^1$ are $R^3$.

61. A method of claim 60 wherein the compound is 6-methoxy-2-(4-methoxyphenyl)-3-[4-(2-piperidinoethoxy)benzoyl]benzo[b]thiophene, or a physiologically acceptable acid addition salt thereof.

62. A method of claim 52 wherein the compound is a compound wherein one of R and $R^1$ is hydrogen.

* * * * *

UNITED STATES PATENT AND TRADEMARK OFFICE
CERTIFICATE OF CORRECTION

PATENT NO. : 4,418,068
DATED : November 29, 1983
INVENTOR(S) : Charles D. Jones

It is certified that error appears in the above—identified patent and that said Letters Patent is hereby corrected as shown below:

In the title the word "ANTIANDRUGENIC" should be spelled ---ANTIANDROGENIC---

In Claim 36, the phrase "R and $R^1$ and $R^3$" should be replaced with ---R and $R^1$ are $R^3$---

Signed and Sealed this

Fifteenth Day of October 1985

[SEAL]

Attest:

DONALD J. QUIGG

Attesting Officer

Commissioner of Patents and Trademarks—Designate